United States Patent
Birnboim et al.

(10) Patent No.: US 10,000,795 B2
(45) Date of Patent: Jun. 19, 2018

(54) STABILIZING COMPOSITIONS AND METHODS FOR EXTRACTION OF RIBONUCLEIC ACID

(71) Applicant: DNA Genotek Inc., Kanata (CA)

(72) Inventors: Hyman Chaim Birnboim, Ottawa (CA); Adele Jackson, Stittsville (CA)

(73) Assignee: DNA GENOTEK INC., Ottawa (CA)

( * ) Notice: Subject to any disclaimer, the term of this patent is extended or adjusted under 35 U.S.C. 154(b) by 0 days. days.

(21) Appl. No.: 15/160,712

(22) Filed: May 20, 2016

(65) Prior Publication Data

US 2016/0340713 A1 Nov. 24, 2016

Related U.S. Application Data

(62) Division of application No. 12/444,447, filed as application No. PCT/CA2007/001785 on Oct. 5, 2007, now abandoned.

(60) Provisional application No. 60/949,778, filed on Jul. 13, 2007, provisional application No. 60/866,985, filed on Nov. 22, 2006, provisional application No. 60/828,563, filed on Oct. 6, 2006.

(51) Int. Cl.
*C12Q 1/68* (2018.01)
*C12N 15/10* (2006.01)

(52) U.S. Cl.
CPC ....... *C12Q 1/6806* (2013.01); *C12N 15/1003* (2013.01)

(58) Field of Classification Search
None
See application file for complete search history.

(56) References Cited

U.S. PATENT DOCUMENTS

| | | | |
|---|---|---|---|
| 5,234,809 A | 8/1993 | Boom et al. | |
| 5,376,527 A | 12/1994 | Robson et al. | |
| 5,512,440 A | 4/1996 | Down et al. | |
| 5,756,126 A | 5/1998 | Burgoyne | |
| 5,939,262 A | 8/1999 | Pasloske et al. | |
| 6,020,186 A | 2/2000 | Henco et al. | |
| 6,071,745 A | 6/2000 | Lin et al. | |
| 6,168,922 B1 | 1/2001 | Harvey et al. | |
| 6,204,375 B1 | 3/2001 | Lader | |
| 6,409,528 B1 | 6/2002 | Bodnar | |
| 6,528,641 B2 | 3/2003 | Lader | |
| 6,602,718 B1 | 8/2003 | Augello et al. | |
| 6,617,170 B2 | 9/2003 | Augello et al. | |
| 6,664,379 B1 | 12/2003 | Kudlicki et al. | |
| 6,777,210 B1 | 8/2004 | Pasloske et al. | |
| 6,825,340 B2 | 11/2004 | Pasloske et al. | |
| 7,001,724 B1 | 2/2006 | Greenfield | |
| 7,005,266 B2 | 2/2006 | Sprenger-Haussels | |
| 7,029,840 B2 | 4/2006 | McMillian | |
| 7,244,828 B2 | 7/2007 | Alam | |
| 7,482,116 B2 | 1/2009 | Birnboim | |
| 8,158,357 B2 | 4/2012 | Birnboim et al. | |
| 8,470,536 B2 | 6/2013 | Birnboim et al. | |
| 2002/0081575 A1 | 6/2002 | Small et al. | |
| 2002/0146677 A1 | 10/2002 | Augello et al. | |
| 2003/0170694 A1 | 9/2003 | Wall et al. | |
| 2005/0019814 A1 | 1/2005 | Laugharn et al. | |
| 2006/0275801 A1 | 12/2006 | Henkin | |
| 2007/0087369 A1 | 4/2007 | Chen et al. | |
| 2009/0162866 A1 | 6/2009 | Birnboim | |
| 2009/0162924 A1 | 6/2009 | Birnboim | |
| 2010/0099149 A1 | 4/2010 | Birnboim et al. | |
| 2010/0273218 A1 | 10/2010 | Birnboim et al. | |
| 2015/0104803 A1 | 4/2015 | Birnboim | |

FOREIGN PATENT DOCUMENTS

| | | |
|---|---|---|
| DE | 10219117 C1 | 10/2003 |
| WO | 1999/000521 A1 | 1/1999 |
| WO | 2003/104251 A2 | 12/2003 |
| WO | 2004/033470 A2 | 4/2004 |
| WO | 2007/068094 A1 | 6/2007 |
| WO | 2007/109586 A2 | 9/2007 |

OTHER PUBLICATIONS

Office Action corresponding to Australian Patent Application No. 2007304776, dated Oct. 7, 2011.
Office Action corresponding to Australian Patent Application No. 2013206564, dated Feb. 10, 2015.
Office Action corresponding to Canadian Patent Application No. 2,664,696, dated Mar. 6, 2015.
Office Action corresponding to Canadian Patent Application No. 2,664,696, dated Dec. 18, 2013.
Office Action corresponding to Israeli Patent Application No. 197916, dated May 9, 2011—English translation.
Office Action corresponding to Israeli Patent Application No. 197916, dated May 16, 2013—English translation.
Office Action corresponding to Israeli Patent Application No. 197916, dated May 22, 2012—English translation.
Office Action corresponding to Israeli Patent Application No. 197916, dated Nov. 19, 2014—English translation.
Office Action corresponding to Japanese Patent Application No. 2009-530744, dated Jul. 2, 2013—English translation.
Office Action corresponding to Japanese Patent Application No. 2009-530744, dispatched Apr. 7, 2015—English translation.
Office Action corresponding to Japanese Patent Application No. 2013229632, dispatched Feb. 3, 2015—English translation.
Office Action corresponding to New Zealand Patent Application No. 576003, dated Aug. 3, 2010.
Office Action corresponding to New Zealand Patent Application No. 576003, dated Jul. 15, 2010.

(Continued)

*Primary Examiner* — Robert M Kelly
(74) *Attorney, Agent, or Firm* — Lathrop Gage LLP; James H. Velema, Esq.

(57) ABSTRACT

The present invention provides a composition and method for stabilizing ribonucleic acid (RNA) from biological samples such that the ribonucleic acid within the sample remains stable at room temperature. The composition comprises an anionic detergent and a buffering agent at a pH of about 5 to about 8.2 and is used in methods for extracting and storing ribonucleic acid from the biological sample.

18 Claims, 17 Drawing Sheets

(56) References Cited

OTHER PUBLICATIONS

Office Action corresponding to New Zealand Patent Application No. 576003, dated Nov. 17, 2011.
Office Action corresponding to European Patent Application No. 07855412.8, dated Apr. 7, 2011.
Summons to attend oral proceedings pursuant to Rule 115(1) of the European Patent Convention corresponding to European Patent Application No. 07855412.8, dated May 15, 2003.
Supplementary European Search Report corresponding to European Patent Application No. 07855412.8, dated Jun. 15, 2010.
Written corresponding to Singapore Patent Application No. 200902344-1, dated Feb. 15, 2011.
Bardon et al. (1980) "Properties of Purified Salivary Ribonuclease, and Salivary Ribonuclease Levels in Children with Cystic Fibrosis and in Heterozygous Carriers," Clinica Chimica Acta. 101:17-24.
Bardon et al. (1984) "Salivary Ribonuclease in Cyctic Fibrosis and Control Subjects," Acta Paediatr. Scand. 73:263-266.
Birnboim (1971) "New Method for Extraction of Ribonucleic Acid and Polyribosomes from Schizosaccharomyces pombe," Journal of Bacteriology. 107(3):659-663.
Birnboim (1992) "Extraction of High Molecular Weight RNA and DNA from Cultured Mammalian Cells," Meth. Enzymol. 216:154-160.
Blumberg (1987) "Creating a ribonuclease-free environment," Methods Enzymol. 152:20-24.
Chu et al. (2004) "Initial viral load and the outcomes of SARS," CMAJ. 171(11):1349-1352.
Croxsom et al. (1981) "Extraction of Rotavirus from Human Feces by Treatment with Lithium Dodecyl Sulfate," Applied and Environmental Microbiology. 41(1):255-260.
Donnelly et al. (2003) "Epidemiological determinants of spread of causal agent of severe acute respiratory syndrome in Hong Kong," The Lancet. 361:1761-1766.
Ehrenfeld et al. (1981) "Stability of Poliovirus RNA in Cell-free Translation Systems Utilizing Two Initiation Sites," The Journal of Biological Chemistry. 256(6):2656-2661.
Eichel et al. (1964) "Acid and Alkaline Ribonucleases of Human Parotid, Submaxillary, and Whole Saliva," Archives of Biochemistry and Biophysics. 107:197-208.
Google Web Page Date of Feb. 1, 2001, downloaded Aug. 25, 2015, https://www.google.com/search?q=sds+tris+edta&rls=com.microsofr/o3Aen-US°/03AIE-Address&source=Int&tbs=cdr%3A1%2Ccd min%3A1%2F1%2F1900%2Ccd_max%3A10%2F6%2F2005&tbm=, "Preparing protein samples for sds-page", No Author, No Volume, No Issue number, 2 page printout.
Google Web Page Date of Feb. 1, 2001, downloaded Aug. 25, 2015, https://www.google.com/search?q=sds+tris+edta&rls=com.microsofr/o3Aen-US°/03AIE-Address&source=Int&tbs=cdr%3A1%2Ccd min%3A1%2F1%2F1900%2Ccd_max%3A10%2F6%2F2005&tbm=, "Preparing protein samples for sds-page", No Author, No Journal, No Volume, No Issue number, 2 page printout.
Grustein (Jun. 8, 2005) "Grunstein Lab Biological Chemistry, Western Membrane Stripping," UCLA. http://www/biolchem.ucla.edu/grunstein/Western%20Membrane%Stripping.html. 1 page.
Guinn (1966) "Extraction of Nucleic Acids from Lyphilized Plant Material," Plant Physiology. 41:689-695.
Guy (2002) "Evaluation of Events Occurring at Mucosal Surfaces: Techniques Used to Collect and Analyze Mucosal Secretions and Cells," Clinical and Diagnostic Laboratory Immunology. 9(4):753-762.
He et al. (2004) "Development of a Western Blot Assay for Detection of Antibodies against Coronavirus Causing Severe Acute Respiratory Syndrome," Clinical and Diagnostic Laboratory Immunology. 11(2):417-422.
http://www.ars.usda.gov/SP2UserFiles/Place/30400510/protocols/WesternBlot.pdf, "Method Used to Extract Total Muscle Protein for Western Blot Using Tris-EDTA Buffer", Published by USDA, Beltsville, MD., Submitted by Wheeler and Ekeren, published Feb. 1, 2001, 13 pages long.
http://www.einsten.net/pdf/1350246084.pdf, "Chem 405 Biochemistry Lab I", published by the University of Texas, Austin, TX, Feb. 1, 2001, downloaded Feb. 22, 2015, Author unknown, no journal, no volume, no issue, 9 pages long.
http://www.google.com/patents/DE10219117C1?cl=en, downloaded Feb. 22, 2015, no author provided, no journal, no issue, no volume, By Google, Inc., Mountain View, California, 4 pages in length.
https://www.google.com/search?q=method+used+to+extract+total+muscle+protein+for+western+blot+using+tris-edta+buffer&rls=com.microsofr/o3Aen-US°/03A1E-Address&tbas=0&biw=1615&bih=845&source=Int&tbs=cdr)/03A1')/02Ccd_mi n%3A1%2 F1')/02F1900')/02Ccd_max')/03A10%2 F6%2 F2005&tbm=, Nov. 17, 2015., Robert Kelly, 2 pages long.
Juusola et al. (2003) "Messenter RNA profiling: a prototype method to supplant conventional methods for body fluid identification," Forensic Science International. 135:85-96.
Kay et al. (1952) "An Improved Preparation of Sodium desoxyribonucleate," Journal of the American Chemical Society. 74(7):1724-1726.
Lee et al. (2006) "Analysis of gene expression profiles of normal human nasal mucosa and nasal polyp tissues by SAGE," J. Allergy Clin. Immunol. 118:134-142.
Li et al. (2004) "RNA Profiling of Cell-free Saliva Using Microarray Technology," J. Dent. Res. 83(3):199-203.
Lindgren et al. (2004) "Noradrenaline represses PPAR (peroxisome-proliferator-activated receptor) g2 gene expression in brown adipocytes: intracellular signalling and effects on PPARg2 and PPARg1 protein levels," Biochem. J. 382:597-605.
Macrae (2007) "Extraction of Plant RNA," Methods in Molecular Biology. 353:15-24.
Moser et al. (2004) "Isolation of Functional RNA From Small Amounts of Different Grape and Applie Tissues," Molecular Biotechnology. 26:95-99.
No Author, Google date search, performed May 5, 2016, https://www.google.com/search?q . . . , Google, San Francisco, CA, 2 pages long.
Okuno et al. (1979) "RNA Polymerase Activity and Protein Synthesis in Brome Mosaic Virus-Infected Protoplasts," Virology. 99:218-225.
Park et al. (2006) "Characterization of RNA in Saliva," Clinical Chemistry. 52(6):1-7.
Peiris et al. (2003) "Clinical progression and viral load in a community outbreak of coronavirus-associated SARS pneumonia: a prospective study," The Lancet. 361:1767-1772.
QIAGEN (2006) "QIAGEN Sample Preparation Systems Offer Guaranteed Freedom of Operation," http://www1.qiagen.com/Products/SamplePrepSystems.aspx.
Rahman et al. (2004) "Chromatography Paper Strip Method for Collection, Transportation, and Storage of Rotavirus RNA in Stool Samples," Journal of Clinical Microbiology. 42(4):1605-1608.
Riddell et al. (2001) "Investigation of Optimal Specimen Type and Sampling Time for Detection of Measles Virus RNA during a Measles Epidemic," Journal of Clinical Microbiology. 39(1):375-376.
Rohan et al. (2000) "Optimization of the Weck-Cel Collection Method for Quantitation of Cytokines in Mucosal Secretions," Clinical and Diagnostic Laboratory Immunology. 7(1):45-48.
Roy et al. (1999) "The effect of saliva specimen collection, handling and storage protocols on hepatitis C virus (HCV) RNA detection by PCR," Oral Diseases. 5:123-127.
Thai et al. (2004) "Development and Evaluation of a Novel Loop-Mediated Isothermal Amplification Method for Rapid Detection of Severe Acute Respiratory Syndrome Coronavirus," Journal of Clinical Microbiology. 42(5):1956-1961.
Van Binnendijk et al. (2003) "Evaluation of Serological and Virological Tests in the Diagnosis of Clinical and Subclinical Measles Virus Infections during an Outbreak of Measles in the Netherlands," The Journal of Infectious Diseases. 188:898-901.
Verwoerd et al. (1989) "A small-scale procedure for the rapid isolation of plant RNAs," Nucleic Acids Res. 17(6):2362.

(56) References Cited

OTHER PUBLICATIONS

Vitale (2001) "The Total RNA Story," Agilent Technologies. Publication No. 5988-2281EN. www.agilent.com/chem.
Wollants et al. (2004) "Evaluation of a norovirus sampling method using sodium dodecyl sulfate/EDTA-pretreated chromatography paper strips," Journal of Virological Methods. 122:45-48.
Wong et al. (2006) "Salivary diagnostics powered by nanotechnologies, proteomics and genomics," J. Am. Dent. Assoc. 137:313-321.
World Health Organization (2003) "A multicentre collaboration to investigate the cause of severe acute respiratory syndrome," The Lancet. 361:1730-1733.
World Health Organization (2006) "Collecting, preserving and shipping specimens for the diagnosis of avian influenza A(H5N1) virus infection, Guide for field operations," Document No. WHO/CDS/EPR/ARO/2006.1, Annex 8.
Yam et al. (2003) "Evaluation of Reverse Transcription-PCR Assays for Rapid Diagnosis of Severe Acute Respiratory Syndrome Associated with a Novel Coronavirus," Journal of Clinical Microbiology. 41(10):4521-4524.
Yamkovaya et al. (2006) "Isolation of Total RNA from Baker's Yeast," Applied Biochemistry and Microbiology. 42(1):84-88.
Zamboni et al. (2008) "Total RNA extraction from strawberry tree (*Arbutus unedo*) and several other woody-plants," iForest. 1:122-125.
International Preliminary Report on Patentability corresponding to International Patent Application No. PCT/CA2007/001785, dated Jan. 19, 2009.
International Search Report with Written Opinion corresponding to International Patent Application No. PCT/CA2007/001785, dated Jan. 21, 2008.

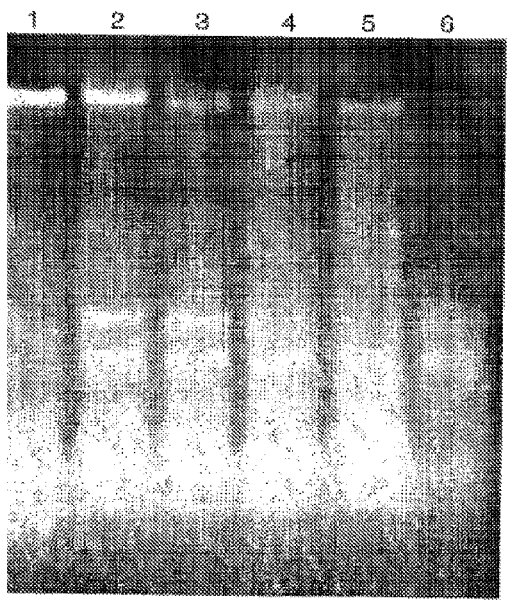 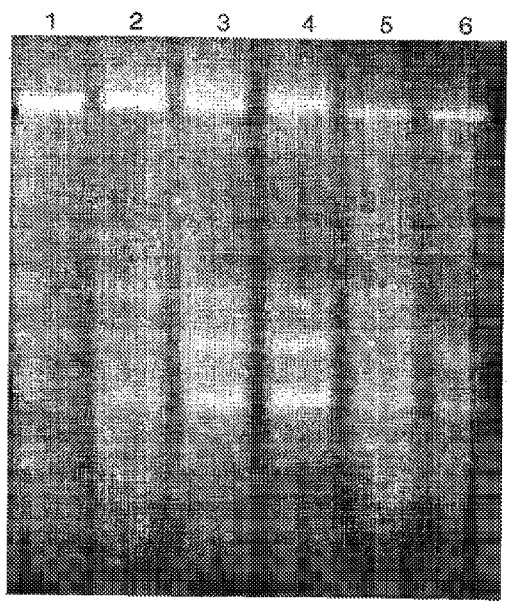
Subject 1  Subject 2
*Fig. 11A*  *Fig. 11B*

STABILIZING COMPOSITIONS AND METHODS FOR EXTRACTION OF RIBONUCLEIC ACID

RELATED APPLICATIONS

This application is a division of U.S. patent application Ser. No. 12/444,447, filed Oct. 22, 2009, now abandoned, which is a 35 U.S.C. § 371 filing of International Patent Application No. PCT/CA2007/001785, filed Oct. 5, 2007, which claims priority to U.S. Provisional Patent Application Nos. 60/828,563; 60/866,985, and 60/949,778 the contents all of which are hereby incorporated by reference in their entirety.

FIELD OF THE INVENTION

The field of the invention generally relates to compositions and methods for storage and/or isolation of ribonucleic acids from bodily fluid(s), and/or secretion(s), (e.g., saliva, mucous), and/or tissue(s).

BACKGROUND

The importance of detection and analysis of ribonucleic acid (RNA) is becoming increasingly evident. For example, a large number of pathogenic mammalian viruses (e.g. SARS-CoA, Influenza virus, Measles virus, Rabies virus, Dengue fever virus, Respiratory Syncytial Virus (RSV), HIV and Hepatitis A, C-E virus) have genomes based on RNA rather than DNA. Detection and/or analysis of such RNA are potentially of great importance, yet an accepted method that is optimal for collecting, preserving/stabilizing, transporting and extracting RNA has not yet been developed.

RNA is a labile compound and the widespread adoption for routine use of RNA as an analyte in detection and analysis of RNA has been limited because of its labile nature. The sugar-phosphate backbone of RNA is particularly sensitive to breakdown (degradation, hydrolysis) by alkaline solutions. It is also sensitive to breakdown by acidic solutions. The pH of maximum stability of RNA is generally assumed to be about neutral, but this has not previously been determined precisely.

RNA can also be degraded enzymatically by endoribonucleases (e.g., pancreatic ribonuclease). Ribonuclease activity has previously been identified in human saliva (Bardon and Shugar, 1980), but the biochemical properties of this enzyme have not been well characterized. Brandon and Shugar (1980) suggest that salivary ribonuclease is pancreatic ribonuclease-like, but this has not been established.

At least in part as result of its instability RNA is often considered as an unsuitable analyte for diagnosis or detection. In the case of RNA viruses, methods have been devised for detection that do not require direct detection of RNA. For example, liquid culturing systems are used to 'grow up' sufficient quantities of virus/bacteria to confirm a diagnosis. Bacterial infection is typically diagnosed by direct staining and microscopic examination of samples. Electron microscopy is also used to identify bacteria and virus containing samples. In serology, diagnosis may be accomplished by detection of antibodies directed against pathogens (e.g. viruses, bacteria, parasites) in blood serum by employing indirect fluorescent antibody testing and enzyme-linked immunosorbent assays Reverse transcriptase PCR (RT-PCR) procedures are sensitive for detecting pathogens, and in some cases before the onset of symptoms. Rapid viral diagnosis will become increasingly critical, both for the control of epidemics and for the management of patients with viral infections. Currently, an immunofluorescence assay (IFA) is considered the "gold standard" for the detection of SARS-CoA infection. However, this test requires culturing of infectious SARS virus in laboratories with biosafety level 3 (BSL-3) facilities by well-trained technician personnel. Hence, there is a need for a more convenient, economical, and low-risk method for collecting and processing infectious clinical specimens.

RNA can be extracted from most, if not all, cell types in the human body (except erythrocytes) and from a variety of cell-containing bodily fluids and/or secretions as well as tissues. In some cases, it is also be desirable to be able to obtain RNA from other sources, including feces, urine, cerebral spinal fluid, animal tissues, bone marrow aspirates, plants, plant extracts, microorganisms, virus, soil samples, sewage, wastewater, and/or foodstuffs (including milk).

Typically, once a RNA-containing sample is collected, it must either be frozen (e.g., with liquid nitrogen) or quickly transported in the unfrozen state at 4° C. to a laboratory for extraction of RNA. The requirement for rapid transportation and/or the requirement of freezing may be problematic in terms of cost and storage space. Additionally, in the case of remote locations and/or large-scale sample collection, rapid transportation and/or freezing may not be feasible. Importantly, rapid processing/testing of clinical samples may not be feasible during an epidemic; back-logged samples will likely degrade over time and/or under sub-optimal storage conditions. A simpler procedure for collecting RNA in a form that would not require the sample be frozen or transported immediately to a laboratory including equipment such as freezers, refrigerators, centrifuges, etc., would be desirable.

As noted above, there are a variety of cellular sources of RNA. Cells from the oral cavity are conveniently obtained from samples of saliva. Saliva can be collected 'passively' by spitting and/or 'actively' with the aid of implements (e.g., swabs). Nasal mucosal samples are conveniently obtained and are a rich source or epithelial and immune cells (e.g., lymphocytes). This procedure is not as invasive compared to, for example, taking of venous blood and a simple procedure based on saliva would permit self-collection by individuals with essentially no prior training. However, once collected, the time that useable RNA can be recovered may be limited because of the presence of ribonucleases in most tissues and bodily fluids.

With the increasing use of nucleic acid-based testing in human and veterinary medicine and in research, there is a need for compositions and methods that would allow RNA to be reliably recovered from bodily fluids and/or secretions and tissues. Desirably, it should be possible to be able to store the collected bodily fluid or bodily tissue at ambient temperature for prolonged periods of time, for example several days or weeks. For example, this would be advantageous where the bodily sample or bodily tissue needs to be shipped to a distant location for purification and analysis, especially in the absence of refrigeration or freezing.

Cationic compounds, such as tetradecyltrimethylammonium oxalate, have been used previously as a component in solutions used in purification of nucleic acids. US20020146677 includes tetradecyltrimethylammonium oxalate plus tartaric acid to stabilize nucleic acid in blood. However, cationic compounds, including tetradecyltrimethylammonium oxalate, have been found to be unsatisfactory in terms of ease of use and long term stability of RNA. It has been found that once the cationic detergent is bound to nucleic acids, the nucleic acids are difficult to dissolve.

In addition, it would be desirable for the amount of RNA in the collected sample to be sufficiently large to allow for the detection of low copy number RNA species such as messenger RNA and some viruses.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a composition and method for prolonged storage of RNA from bodily fluids and/or tissues at room temperature, which compositions and methods further facilitate extraction of the RNA in as high a yield and as nearly intact state as is possible.

In accordance with one aspect of the present invention there is provided a composition for extracting and storing ribonucleic acid from a sample such that the ribonucleic acid within said sample remains stable at room temperature, said composition comprises: an anionic detergent; and a buffering agent at a pH of about 5 to about 8.2; wherein said composition stabilizes said ribonucleic acid at room temperature.

In accordance with another aspect of the present invention there is provided a method for preserving ribonucleic acid from a biological sample comprising the steps of: a. obtaining the sample from a subject; b. contacting said sample with a composition comprising an anionic denaturing agent and a buffering agent at a pH of about 5 to about 8.2 to form a mixture; c. storing the mixture at room temperature; and d. heating the mixture at greater than or about equal to 50° C. prior to subsequent processing, wherein said composition stabilizes said ribonucleic acid at room temperature.

In accordance with another aspect of the present invention there is provided a RNA storage kit, comprising: a. a composition according to the present invention.

BRIEF DESCRIPTION OF THE FIGURES

FIG. 11A-B are photographs of ethidium bromide-stained, transilluminated agarose gels showing the results of electrophoresis of RNA samples stored in compositions of the present invention and heated at various temperatures subsequent to storage at room temperature; subject 1 (FIG. 11A) and subject 2 (FIG. 11B);

DETAILED DESCRIPTION OF THE INVENTION

Figure 1:
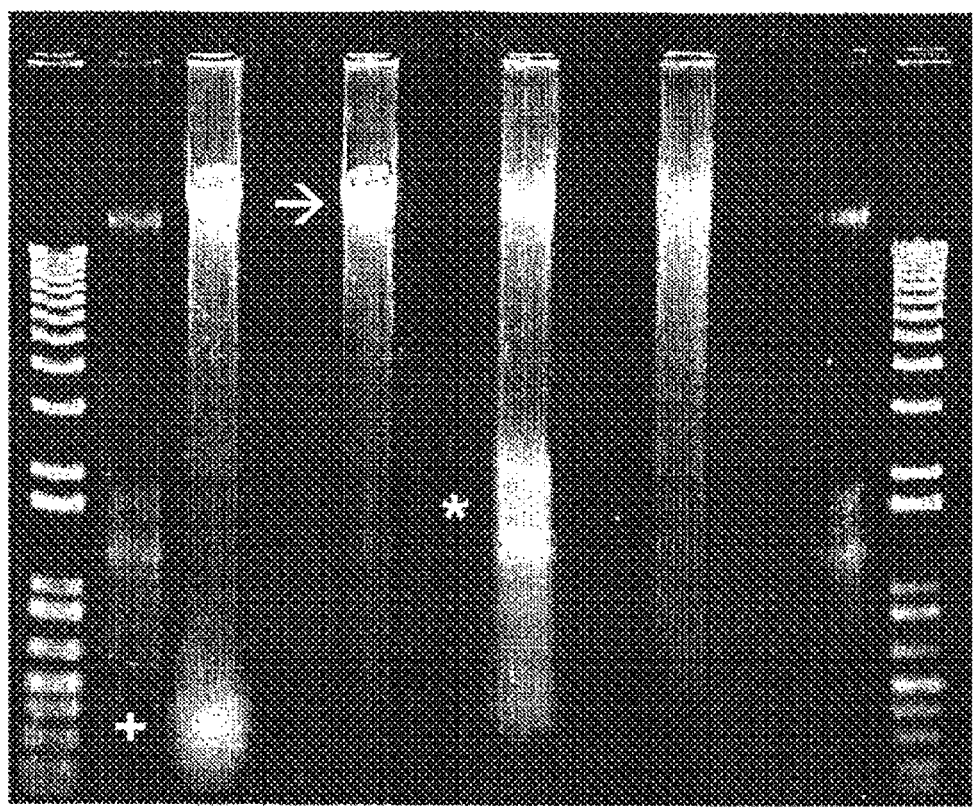
FIG. 1 is a photograph of an ethidium bromide-stained, transilluminated agarose gel showing the results of electrophoresis of nucleic acids from saliva stored in compositions of the present invention and stored in Oragene™.

As will be described in more detail below, the present invention relates to compositions and methods for prolonged storage, and extraction, of ribonucleic acid (RNA) from bodily fluids such as saliva, nasal secretions and/or tissues, wherein the RNA in the resulting composition remains stable at room temperature for extended periods of time.

The term "about", as used herein, refers to +/−10% of the stated value or a chemical or obvious equivalent thereof.

The term "bodily fluid", as used herein, refers to a naturally occurring fluid from a human or an animal, and includes, but is not limited to saliva, sputum, serum, plasma, blood, pharyngeal, nasal/nasal pharyngeal and sinus secretions, urine, mucous, gastric juices, pancreatic juices, bone marrow aspirates, cerebral spinal fluid, feces, semen, products of lactation or menstruation, cervical secretions, vaginal fluid, tears, or lymph.

The terms "bodily tissue" or "tissue", as used herein, refer to an aggregate of cells usually of a particular kind together with their intercellular substance that form one of the structural materials of a plant or an animal and that in animals include connective tissue, epithelium, mucosal membrane, muscle tissue, and nerve tissue, and the like.

The term "Ct value", as used herein, is as defined in the Operator Manual for our Rotor-Gene™ 6000 (real-time genetic amplification detection system; manufactured by Corbett Life Science) and refers to the fractional cycle number at the point where the amplification curve crosses a threshold of detection. By setting a threshold line and calculating the intersection with each of the sample curves, the Ct values for each sample are established. The threshold line is set in the exponential phase of the run, significantly above the background level to avoid noise and below the onset of signal plateau in later cycles.

The term "nucleic acid", as used herein, refers to a chain of nucleotides, including deoxyribonucleic acid (DNA) or ribonucleic acid (RNA), typically found in chromosomes, chromatin, mitochondria, ribosomes, cytoplasm, nucleus, microorganisms (e.g., bacteria) or viruses.

The term "ribonucleic acid" or "RNA", as used herein, refers to a wide range of RNA species, including, but not limited to high molecular RNA, large and small ribosomal RNAs, messenger RNA, pre-messenger RNA, small regulatory RNAs, RNA viruses (single and double-stranded, positive stranded or negative stranded) and the like. The RNA may be from a variety of sources, including, but not limited to human, non-human, viral, bacterial, fungal, protozoan, parasitic, single-celled, multi-cellular, in vitro, in vivo, natural, and/or synthetic sources.

The term "primer", as used herein, refers to an oligonucleotide acting as a starting point from which the synthesis begins in the presence of a DNA template or a RNA template, reagents for polymerization and so on. Although a primer is preferably single-stranded, double-stranded primers may also be used. When double-stranded primers are used, it is desirable to convert them into their single-stranded forms before use in an amplification reaction. A primer may be chemically or enzymatically synthesized using well known methods, or may be isolated from an organism.

The term "saliva", as used herein, refers to the secretion, or combination of secretions, from any of the salivary glands, including the parotid, submaxillary, and sublingual glands, optionally mixed with the secretions from the numerous small labial, buccal, and palatal glands that line the mouth.

The term "sputum", as used herein, refers to mucoid matter contained in or discharged from the nasal or buccal cavity of a mammal, including saliva and discharges from the respiratory passages, including the lungs.

The term "subject", as used herein, refers to a variety of organisms/sources, including, but not limited to human, non-human mammals, other animal species, viral, bacterial, fungal, protozoan, parasitic, single-celled, multi-cellular, in vitro, in vivo, natural, and/or synthetic sources. Specific non-limiting examples of suitable subjects include human and bovine sources. Specific non-limiting examples include beef cattle, dairy cattle, sheep, goats, hogs, poultry and horses. Specific non-limiting examples also include companion animals, such as dogs, cats and the like.

The term "prolonged storage" refers to storage for at least about one day, two days, three days, four days, six days, one week, two weeks, three weeks, four weeks, five weeks, six weeks, seven weeks, or eight weeks, from about one day to about eight weeks, or greater than about eight weeks.

Composition

The composition of the present invention is a composition for extracting RNA from a bodily fluid or tissue and maintaining the RNA contained therein stable at room temperature for prolonged periods.

As will be discussed in more detail below, the composition of the present invention includes an anionic detergent and a buffer.

Selection of the specific components of the composition is made based on various criteria, including, for example, efficacy for stabilizing ribonucleic acid, cost, safety for the subject and the laboratory worker, availability, and compatibility with downstream applications. The choice of the components and their concentration should be appropriate to stabilize the RNA in the biological sample at room temperature.

The composition of the present invention permits storage of the sample at room temperature and subsequent processing to isolate and purify the RNA contained therein. The term "processing" as used herein refers to mechanical or chemical steps used to isolate or purify the ribonucleic acid from composition mixed with biological sample.

A major cause of nucleic acid instability in biological samples is the presence of deoxyribonucleases and ribonucleases. Deoxyribonucleases and ribonucleases are enzymes that break down DNA or RNA, respectively. Their main source in the digestive tract is secretions of the pancreas, although these enzymes may also be present in secretions and cells of the salivary gland and buccal mucosa. In addition, microorganisms resident in the mouth or from recently ingested foods may release deoxyribonucleases or ribonucleases. Over time, the nucleic acid within a biological sample (e.g., saliva) stored in water would be expected to degrade or break down.

The compositions of the present invention provides inhibition of nucleases, including ribonucleases, and chemical stabilization of RNA. Ribonuclease inhibition and the ability to store a ribonuclease-containing RNA sample at room temperature is achieved through the use of an anionic detergent and a buffer wherein the appropriate pH is maintained, followed by an incubation step at about 50° C. or above, prior to subsequent processing of samples. Optionally, proteinase K is included in the incubation step. An appropriate pH, as used herein, is (i) a pH at which RNase activity is minimized or eliminated and (ii) a pH at which RNA remains chemically stable.

Anionic Detergent

While not wishing to be bound by theory, it is thought that action of deoxyribonucleases and ribonucleases is inhibited by anionic detergents that destroy their complex structure, particularly their catalytic sites. Hence, anionic detergents can be included in the composition of the present invention. Non-limiting examples of suitable anionic detergents include sodium dodecyl sulfate (SDS), sodium sarcosinate (sarkosyl), lithium dodecyl sulfate, sodium 1-octane sulfonic acid, and the like.

In accordance with a specific embodiment of the present invention, the composition contains the anionic detergent SDS at a concentration such as when it is mixed with saliva, the SDS is in the range of about 0.5% to about 8%. In another example, the composition contains the anionic detergent SDS at a concentration such as when it is mixed with saliva, the denaturing agent is in the range of about 1% to about 8% or 2% to about 8%.

In one example, the composition contains the denaturing agent Sarkosyl at a concentration such that when it is mixed with saliva, the concentration of sarkosyl is in the range of about 0.5% to about 8%. In another example, the concentration of sarkosyl is in the range of about 2% to about 4%.

Buffer

In accordance with one embodiment of the present invention, the composition comprises an anionic detergent and a buffer to maintain the pH within the range of 5-8.2. In accordance with another embodiment of the present invention, the composition comprises a denaturing agent and a buffer to maintain the pH within the range of 5.1-7.0. In one example, the pH of the composition is in the range of about 5.5 to about 7.5. In one example, the pH of the composition is in the range of about 6.5 to about 7.0. In one example, the pH of the composition is about 6.8. The pH of the composition can be maintained at the desired pH using a buffer.

Non-limiting examples of suitable buffering agents include sodium cyclohexane diaminetetraacetate (CDTA), N,N-bis(2-hydroxyethyl)-2-aminoethanesulfonic acid (BES), 4-(2-Hydroxyethyl)piperazine-1-ethanesulfonic acid (HEPES), acetic acid or acetate (e.g. sodium acetate), citric acid or citrate, malic acid, phthalic acid, succinic acid, histidine, pyrophosphoric acid, maleic acid, cacodylic acid, ββ'-Dimethylglutaric acid, carbonic acid or carbonate, 5(4)-Hydroxymethylimidazole, glycerol 2-phosphoric acid, ethylenediamine, imidazole, arsenic acid, phosphoric acid or phosphate, sodium acetate, 2:4:6-collidine, 5(4)-methylimidazole, N-ethylmorpholine, triethanolamine, diethylbarbituric acid, tris(hydroxymethyl)aminomethane (Tris), 3-(N-Morpholino)propanesulfonic acid, 4-morpholinepropanesulfonic acid (MOPS), 2-morpholinoethanesulfonic acid (MES), piperazine-1,4-bis(2-ethanesulfonic acid) (PIPES), N-[tris(hydroxymethyl)methyl]-2-aminoethanesulfonic acid (TES), 4-(2-Hydroxyethyl)piperazine-1-propanesulfonic acid (EPPS), N-(2-acetamido)-2-aminoethanesulfonic acid (ACES), or combinations thereof. Other examples include phosphate, carbonate, ethylenediamine or imidazole buffers.

Additional non-limiting examples of suitable buffering agent include buffering agents having a pKa at 25° C. of from about 4.7 to about 8.0.

In a specific example the buffer is CDTA. In another example the buffer is citrate/citric acid.

The following are non-limiting examples of compositions according to the present invention.

In accordance with a specific example, the composition comprises 4% SDS, 50 mM CDTA adjusted to pH 6.2.

In accordance with a specific example, the composition comprises 4% SDS, 50 mM CDTA adjusted to pH 6.6.

In accordance with a specific example, the composition comprises: 16% SDS or 12% SDS or 8% SDS, 50 mM CDTA buffered to pH 6.2.

In accordance with a specific example, the composition comprises 1% SDS, 50 mM CDTA adjusted to pH 6.6.

In accordance with a specific example, the composition comprises 4% SDS, 50 mM citric acid buffered to pH 6.6.

In accordance with a specific example, the composition comprises 4% Sarkosyl, 50 mM CDTA buffered to pH 6.6. In another example the composition comprises 8% Sarkosyl, 50 mM CDTA buffered to pH 6.6.

In accordance with a specific example, the composition comprises 4% SDS, 50 mM LiCDTA, 250 mM LiCl adjusted to pH 6.8.

Surprisingly, it has been found that the composition of the present invention can stabilize RNA, such as high molecular weight RNA, present in biological samples such as sputum or saliva or nasal, anterior nasal, and/or nasopharyngeal samples for prolonged periods of time at room temperature. Notably, the RNA can be purified using a variety of methods, and can be purified without a requirement for phenol extraction, guanidinium salts, or any column or binding matrix. The purified RNA is sufficiently pure to be used directly in downstream applications such as, for example, the preparation of complementary DNA (cDNA). However, phenol extraction, guanidinium salts, or any column or binding matrix may be used, if desired.

While not wishing to be bound by theory, in the case of the specific example noted supra, it is believed that the anionic detergent, for example SDS binds, denatures and inhibits salivary ribonuclease(s) and the buffer, for example CDTA, keeps the pH of the saliva sample neutral or slightly acidic. Buffering the sample in a relatively narrow range helps to ensure the RNA is chemically stable, despite the fact that ribonuclease(s), such as salivary ribonuclease(s), are potentially active in this pH range. While salivary RNA is stable for extended periods of time (e.g., weeks to months) in this composition, it has been discovered that salivary ribonuclease activity is robust in some samples may not be permanently inactivated. Once the constraints of SDS have been removed during subsequent processing/purification (e.g., if the composition of the present application is diluted below a certain concentration (e.g., below 0.5% SDS), the RNA within the sample may be substantially degraded.

The Applicant has surprisingly discovered that heating the sample at temperatures above about 50° C. following storage at room temperature and prior to subsequent processing allows the RNA within the sample to be extracted in a substantially intact form. Again, while not wishing to be bound by theory, it appears that this heating step largely or completely inactivates salivary ribonuclease activity while assisting in the liberation of RNA from cells. The optional step of adding proteinase K to the biological sample in this composition during the heating step, prior to purification, helps digest proteins in the saliva and may also contribute to the inactivation of salivary ribonuclease activity.

In optimizing the components of one embodiment of the composition of the present invention, the Applicant has determined a pH range that, on the one hand, is optimal for minimizing chemical degradation of the RNA and, on the other hand, permits SDS to strongly inhibit the salivary ribonuclease activity. The composition of the present application reduces ribonuclease activity nearly completely while maintaining the chemical stability of RNA.

In accordance with a specific example of the present invention, the denaturing agent is not a guanidinium salt.

It has been found that RNA extracted and stored using the compositions of the present invention is substantially intact, suitable for RT-PCR analysis, and is recoverable from samples without the aid of any nucleic acid-binding matrix such as paramagnetic silica-coated beads or a silica-based membrane.

In one example, the method of the present invention promotes recovery of intact, high molecular weight RNA.

Method

In accordance with another aspect of the present invention, there is provided a method for storing RNA for prolonged periods at room temperature.

Samples may be obtained from variety of sources including, but not limited to humans, non-human primates, livestock (e.g., cattle, pigs, sheep, goats, domestic birds such as chicken, turkey, pheasant, duck, geese), game and wild animals (e.g., deer, elk, moose, fish, birds, bear), laboratory and companion animals (e.g., non-human primates, rodents such as mice, rats, rabbits, guinea pigs, gerbils, hamsters), pigs, goats, sheep, dogs, cats, fish, snakes, lizards, turtles, a horse and the like. Samples may also be obtained from plants, cell lines, soil microorganisms, sewage microorganisms, pathogenic microorganisms (e.g, virus, bacteria, parasites) and the like.

In specific example, the sample is obtained from a human source. In an alternate specific example, the sample is obtained from a bovine source.

In a specific example, the RNA is within saliva. The method comprises the steps of mixing a sample of saliva with the composition of the present invention, then storing the saliva-composition mixture at room temperature. In one example, The method comprises the steps of mixing a sample of saliva with approximately an equal volume of the composition of the present invention, then storing the saliva-composition mixture at room temperature. Prior to subsequent processing, the sample is heated above about 50° C. for a short period of time.

In an alternate specific example, the RNA is within a nasal, anterior nasal and/or nasopharyngeal sample. The method comprises the steps of mixing the nasal, anterior nasal and/or nasopharyngeal sample with the composition of the present invention, then storing the mixture at room temperature. The RNA is stable for at least about one day and at least about four weeks. Prior to subsequent processing, the sample is heated above 50° C. for a short period of time.

Advantages to the subject of providing a saliva sample or nasal, anterior nasal and/or nasopharyngeal sample, rather than a blood sample as a source of ribonucleic acid, include that subjects typically prefer avoiding the discomfort, pain and apprehension associated with phlebotomy. Additionally, and although use of a pin-prick to obtain a drop of blood is sufficient to recover a useable amount of DNA, the expected amount of RNA is too small to be useable for most purposes. Saliva, sputum, nasal, anterior nasal and/or nasopharyngeal samples have a further advantage of not requiring specialized personnel for collection, thereby reducing cost where mass sample collection is being carried out (e.g., during a epidemic/pandemic). However, it will be clear to the skilled worker that while saliva is one source of RNA, other bodily fluids, including blood, and bodily tissues, can be used. The present invention is not intended to be limited to the collection and storage of RNA obtained from sputum, saliva, nasal, anterior nasal and/or nasopharyngeal samples.

To collect saliva from a subject it is preferred that the mouth be rinsed before sampling. Food particles can introduce foreign RNA and saliva transferred by kissing can be a source of foreign human RNA or viral RNA. The mouth can be rinsed with about 50 ml of tepid water by vigorous swishing or by brushing with a toothbrush without toothpaste. Unstimulated saliva is usually of the mucinous type and is secreted at a slow rate. Stimulated saliva (anticipation of tasty food, sweet or sour candy) is of the serous (watery) type and secreted at a faster rate. After rinsing of the mouth and waiting about 5 minutes for the mouth to clear of water, the subject may spit a volume (for example, about 1-2 ml) of saliva, preferably stimulated saliva, into the receiving tube. Saliva flow can conveniently be stimulated with a few grains/pinch of table sugar placed on top of the tongue, or any other such saliva-stimulatory substance that does not interfere with RNA stability or subsequent amplification.

Saliva may also be obtained from subjects such as infants, young children and people with disabilities and/or illness that may be unable to directly spit into a collection device. In this instance, an implement (e.g., a swab etc.) is used to collect saliva.

Saliva may also be obtained from non-human animals such as livestock, companion animals and the like, which may be unable or unwilling to directly spit into a collection device. In this instance, an implement (e.g., a swab etc.) is used to collect saliva.

To collect anterior nasal or nasopharyngeal samples from a subject, a variety of implements may be used. Mucosal cells can be scraped using rigid or flexible brushes, swabs, or plastic/wood scrapers and cells may be flushed from the nasal cavity by introducing a liquid (e.g., saline) and recovering the liquid. For example, a rigid swab/brush can be placed in the anterior of the nose and a flexible swab/brush into the posterior nasopharyngeal cavity and used to collect mucosal secretions and to gently rub off cells from the mucosal membrane. Samples collected with said liquid and/or implement(s) can be delivered into a collection device containing the composition of the present invention. In situations where it is desirable to introduce a volume of said liquid that is greater than the volume of the composition, a correspondingly larger amount of composition of the present invention would be provided. A cutting device (e.g. scissors) may be used to shorten the length of a swab's/applicator's handle to permit closure of the collection device. Alternately, swabs or brushes with handles that snap under pressure, as well as swabs or brushes with a moulded breakpoint in the handle/shaft, can be used to facilitate sample collection. The 'full length' handle facilitates the collection of a sample and shortening of the swab/brush at the engineered break point permits a better fit into the collection device. It is also feasible to recover RNA from tissue samples taken from the nasal cavity. Fresh tissue specimens/biopsies (e.g., normal nasal mucosa or nasal polyp tissue) obtained from patients undergoing rhinoplasty or endoscopic sinus surgery can be collected in the composition of the present invention for subsequent RNA isolation.

Methods of the invention are conveniently practiced by providing the compositions used in such method in the form of a kit. Such a kit preferably contains appropriate composition and may include swabs to facilitate sample collection. At least one type of positive control or standard may be provided that can be a nucleic acid (DNA or RNA) template for demonstrating the suitability of the sample for the detection of a target gene or nucleic acid sequence (e.g. transcript). Such a kit preferably contains instructions for the use there of.

Optionally, the kit includes a container, such as that described in International PCT Application No. WO 03/104251, the contents of which are incorporated herein by reference in its entirety.

Optionally, the kit includes a container, such as that described in U.S. Application Ser. No. 60/748,977, or PCT/CA2006/002009 the contents both of which are incorporated herein by reference in their entirety.

Optionally, the kit includes a collection assembly, such as that described in PCT/US2007/64240, the contents of which are incorporated herein by reference in its entirety.

Desirably, the container facilitates collection in the field, without the requirement of a clinic or hospital, and is sized to be mailed to a collection site and/or an analysis site.

Applications

The compositions and methods of the present invention are suitable for use in a wide range of applications.

With the continuing concern about respiratory viral/bacterial epidemics/pandemics, the methods and compositions of the present invention are expected to be valuable for the wide-scale field collection, transport, storage, purification and subsequent analysis in a diagnostic laboratory of biological samples, such as nasal, nasopharyngeal, sputum and/or saliva samples. Stability of said samples in the composition of the present invention at room temperature is expected to be extremely valuable in situations (e.g. epidemics) when laboratories are overwhelmed with large numbers of patient samples.

Additionally, with the increased importance and requirement of livestock monitoring and tracking, the compositions and methods of the present application are suitable for collection, storage and archiving of livestock samples for disease surveillance and livestock monitoring. The compositions and methods of the present application are also suitable for use with companion animals, such as dogs, cats, and the like.

Saliva is expected to surpass blood as the sample of choice for many clinical diagnostic and genetic tests. Generally, a sputum, saliva, nasal, anterior nasal and/or nasopharyngeal sample is a less hazardous specimen to collect and process than blood; both saliva collection and nasal, anterior nasal and/or nasopharyngeal collection is non-invasive or minimally-invasive for the patient and can be easily collected on multiple occasions. Generally, such sample collection does not require a skilled technician.

Nasal, anterior nasal and nasopharyngeal samples have been shown herein to be suitable for use with the methods and compositions of the present invention.

The nasal cavity is considered part of the upper respiratory tract. Nasal mucosa is a rich source of epithelial and immune cells (e.g. lymphocytes). Airway mucosa (nasal cavity and lungs) is the first site of exposure to inhaled pathogens (e.g. bacteria and virus). T cells present in respiratory mucosa are believed to play an important role in the regulation of mucosal immune responses to foreign antigens (e.g. infectious microbial antigens) bombarding the mucosal surface.

Respiratory viruses (e.g. Respiratory Syncytial Virus, RSV) infect, replicate and are shed from respiratory mucosa; transmitted to others via nose and mouth. RSV causes serious respiratory infection in young children.

Nasal samples stabilized in the composition of the present invention are useful for the analysis of gene expression profiles of normal nasal mucosa and nasal polyp tissue to understand the pathophysiology of a variety of rhinopathies/inflammatory diseases (1).

Assessment of mucosal secretions/samples (saliva and nasal samples) can provide important insights into mucosal (and systemic) humoral and cellular responses induced by infection and/or immunization (2, 9).

Both saliva and nasal samples collected into the composition of the present invention can also be used for the diagnosis/identification of pathogen(s), e.g. SARS-CoA, RSV, measles virus, influenza virus, rabies virus, Dengue fever virus, HIV, Hepatitis A, Hepatitis C-E virus, Mycobacterium, etc.

It is also increasingly important and desirable to detect and/or analyze RNA from animals. The methods and compositions of the present invention are suitable to use for the diagnosis and/or identification of RNA viruses which infect livestock include. Non-limiting examples include: foot-and-mouth disease virus (FMDV) (which infects domesticated and wild ruminants and pigs; most commonly spread of infection via inhalation of infectious droplets originating in breath of infected animals); bovine leukosis virus (BLV); bovine parainfluenza virus (e.g. Parainfluenza-3 virus, PI-3); bovine respiratory syncytial virus (BRSV); porcine reproductive and respiratory syndrome virus; vesicular stomatitis virus; bovine viral diarrhea virus (aerosol infection); bovine coronavirus (e.g. SARS-associated coronavirus (SARS-CoV)); BHV1 virus (bovine rhinotracheitis, respiratory disease); equine arteritis virus (aerosol infection); Nipah virus (porcine respiratory and neurologic syndrome); Porcine Respiratory Corona Virus Infection (PRCV); rabies virus (mammals); Jaagsiekte Sheep Retrovirus (contagious lung cancer in sheep); infectious bronchitis virus (IBV) (poultry); avian pneumovirus (APV) (poultry); newcastle disease virus (NDV) (poultry respiratory, nervous, and digestive systems); Influenzavirus A (Avian influenza) subtype H5N1 ("avian flu").

The methods and compositions of the present invention are suitable for the stabilization and subsequent detection/analysis of ribonucleic acids from bacteria, fungi, cells infected with virus, isolated virus, tissue cultures, cell lines and bodily fluids and/or tissues that are contaminated with, or suspected of being contaminated with, virus, bacterial, protozoa, fungi and the like, and combinations thereof.

Additionally, the compositions and methods of the present invention are suitable for use in cytoplasmic, nuclear and/or mitochondrial RNA stability and analysis, archival (e.g., banking) of samples (fluids and/or tissues), tracking the source for the RNA (e.g. placental/fetal versus maternal origin), tracing the lineage of the ribonucleic acid (e.g. identification and characterization of the infected source and subsequent transmission pathways of a virus).

Additionally, desirably the compositions of the present invention render pathogens (viruses and bacteria) non-infectious, making for safe handling of clinical samples. This is particularly the case once samples have been heated. In contrast, clinical specimens collected in 'traditional' sterile transport medium (e.g., Viral transport media (VTM)—Annex 8. "Collecting, preserving and shipping specimens for the diagnosis of avian influenza A (H5N1) virus infection Guide for field operations, October 2006. WHO) and suspected of containing a pathogen(s) must be processed in biosafety level 3 or 4 containment facilities. These facilities are not numerous and would be overwhelmed in the event of an epidemic. Moreover, remote areas, e.g. some countries in Africa, do not have biosafety level 3 or 4 containment facilities/laboratories.

The compositions and methods of the present invention are suited to collection and isolation of RNA from healthy and infected individuals in the field, over wide geographical areas, which can provide vital surveillance information for the prediction and prevention of large-scale epidemics. Such samples would be invaluable for identifying candidate vaccine strains and identification of virus genotypes for molecular epidemiological studies.

The compositions and methods of the present invention are suitable for diagnosis of an infection in the early phase of an illness (e.g., before seroconversion). This aspect is important for 1) managing patient care and improving disease outcome, and 2) preventing/reducing transmission. The sensitivity of 'traditional' serological testing (as noted above) is too low for early detection of infection. For instance, SARS-CoA can not be detected by this traditional method until 14-28 days after the onset of symptoms (e.g. fever). To address the need for early and rapid identification of SARS-CoA, a reverse transcription (RT)-PCR-based assay was advocated by the World Health Organization (WHO) and is being routinely used for detecting virus-specific RNA (4, 5). More recently, a loop-mediated isothermal amplification method for rapid detection of severe acute respiratory syndrome coronavirus has been developed (3). While significant progress has been made in PCR-based diagnostic techniques, the success of these assays relies heavily upon the collection of clinical specimens into sterile transport medium and rapid transport to biosafety level 3/4 containment facilities at 4° C. for immediate processing. Typically, these samples are collected from patients already admitted to hospital and precious time (days) is often 'wasted' replicating the virus in cell cultures, followed by monitoring for cytopathic effects. As discussed above, the 'traditional' methods of sample collection into transport medium is inadequate during an epidemic/pandemic when diagnostic laboratories would be overwhelmed with samples. Laboratories have limited capacities for refrigerating and/or freezing samples, so the degradation of backlogged samples during an epidemic would be anticipated. Samples would need to be recollected and precious time would be wasted.

The compositions and methods of the present invention, in combination with RT-PCR, are also suitable for use in the diagnosis of subclinical disease. For instance, in the Netherlands, RT-PCR tests have detected measles virus (MV) RNA in throat-swab specimens from 5 days BEFORE until 12 days after the onset of rash (7). "Oral fluid proved to be the most practical specimen for the simultaneous detection of MV-specific IgM antibody and viral RNA. Viral RNA was also detected in oropharyngeal specimens from 3 healthy contact persons with serological proof of MV infection." Hence, samples collected from the nasal and oral cavity can be used for the diagnosis of clinical and subclinical MV infection. Similar findings were reported by another group studying a measles outbreak in the state of Victoria in Australia in 1999 (8). Of lymphocytes (peripheral blood leukocytes), urine, throat swab, and serum specimens, throat swab specimens were optimal/the preferred specimen for detection of measles virus RNA during the first 2 weeks after the rash. In this case, the tip of the throat swab was placed in 3 mL of sterile viral transport medium and was transported to the laboratory at 4° C.

While great strides have recently been made in the field of diagnostic testing (i.e. RT-PCR tests), clinical specimens are still collected into 'sterile transport medium' (e.g., VTM described supra) and thus extremely labile. Since RNA (human and/or bacterial and/or viral transcript) in this type of medium will most likely degrade in transit, the expression profile of the sample once it reaches the diagnostic laboratory will not accurately reflect the profile of the patient at the time of collection. There is also a high probability that infectious agents within these clinical samples are still infectious after transport to the lab.

To gain a better understanding of the invention described herein, the following examples are set forth. It should be understood that these examples are for illustrative purposes only. Therefore, they should not limit the scope of this invention in any way.

EXAMPLES

Example 1: Protocol for Obtaining Saliva Samples from Human Subjects

The subject is instructed to wait for a period of 30-60 minutes before last eating. If possible, the subject will brush his teeth (without using toothpaste). If possible, the subject will rinse his/her mouth with 50 ml of water. The subject will be requested to wait for 5-10 minutes to allow the mouth to clear of water. For subjects able to spit, they will be instructed to spit saliva into the special collection tube until the level of saliva reaches the 1 or 2 ml mark. Waiting after last eating and rinsing the mouth is desirable but not essential. Collection of saliva may take several minutes. If the subject finds that he/she is unable to deliver sufficient saliva, he/she will be given a few grains of table sugar to chew or place on the top of their tongue, and told not to be concerned if some of the sugar is spit into the tube. For subjects unable to spit (e.g., infants, young children, individuals with limitations/disabilities), an implement (e.g., swab, brush, transfer pipette) may be used, along with sugar, for sample collection. Similarly, a subject may be provided a liquid (e.g., mouthwash, water, saline) to gargle his/her mouth and throat or saline to flush his/her nasal cavity. Samples collected with said liquid would be delivered into the collection tube. In situations where the saliva/sputum/nasal secretions have been substantially diluted by said liquid, a correspondingly larger amount of composition of the present invention would be provided.

Where two or more samples are to be taken from a subject for purposes of comparing two compositions, the subject is asked to deliver small amounts of saliva alternating between two or more tubes until each tube is filled to the 1 ml mark. This is necessary because the composition of saliva from the subject can vary during the process of spitting.

When the required amount of saliva is collected, it is immediately mixed with an equal volume of a composition. The precise way in which this will be introduced will depend upon the container design. Once the saliva is introduced and mixed with the composition, the container is securely capped. The RNA-containing sample can be maintained at room temperature for prolonged periods of time. A portion of the RNA-containing sample in aqueous solution can be used as a RNA template for a reverse transcription reaction to produce complementary DNA (cDNA), which can then be used in a PCR reaction.

Example 2: Comparison of the Present Composition to Oragene™

Sample Collection

In this example, a single subject provided two sputum/saliva samples (2 ml each) within a short period of time. One sample was collected into a vial containing 2 ml of a composition of the present invention comprising: 4% SDS, 50 mM CDTA, pH 6.6. Shortly afterwards, the same subject provided a second sample into a vial containing 2 ml of Oragene™ solution. Samples were shaken and left at room temperature (RT) for 3 days before purification of nucleic acids.

Methods

Nucleic acids were purified from this subject's saliva in Oragene™ or in the composition of the present invention. A portion of the subject's sample in Oragene™ was mixed with proteinase K and heated at 50° C. for 2 hours, without (FIGS. 1 and 2) and with (FIG. 2) an additional, subsequent heating at 90° C. for 15 minutes. A portion of the subject's sample in the composition was mixed with proteinase K, heated at 50° C. for 2 hours and then at 90° C. for 15 minutes (FIG. 1). The inclusion of a short incubation at a temperature above 50° C. was found to be necessary for some saliva samples to facilitate the extraction of intact, high molecular weight RNA from saliva collected in the composition of the present invention, but had no effect on saliva collected in Oragene™.

Samples were then centrifuged briefly to remove insoluble material and the DNA and RNA remaining in the supernatant was precipitated with 2 volumes of 95% ethanol. The precipitate was dissolved in an appropriate buffer containing 0.1% SDS and a 10 µl aliquot (equivalent to about 10 µl of undiluted saliva) was analyzed by electrophoresis on a 0.9% agarose gel, and then stained with ethidium bromide (1 µg/mL) to visualize the DNA and RNA (see FIGS. 1 and 2). A 10 µL aliquot of each purified sample was also treated with pancreatic ribonuclease before gel electrophoresis to demonstrate that the high molecular weight material stabilized in and extracted from the composition of the present invention is, RNA (FIG. 1). Note that in FIG. 1, genomic high molecular weight DNA present in the saliva sample is indicated by an arrow (→), the characteristic ribosomal RNA doublet is indicated by an asterisk (*), and low molecular weight RNA is represented by a plus sign (+).

The sample order of FIG. 1 is as follows:

| Lane | Sample |
| --- | --- |
| 1 | 1 Kb+ DNA ladder |
| 2 | RNA marker |
| 3 | Nucleic acids purified from saliva in Oragene ™ |
| 4 | Blank lane |
| 5 | Purified sample (see lane 3) treated with ribonuclease prior to gel electrophoresis. |
| 6 | Blank lane |
| 7 | Nucleic acids purified from saliva in a composition of the present invention. |
| 8 | Blank lane |
| 9 | Purified sample (see lane 7) treated with ribonuclease prior to gel electrophoresis. |
| 10 | Blank lane |
| 11 | RNA marker |
| 12 | 1 Kb+ DNA ladder |

Figure 2:
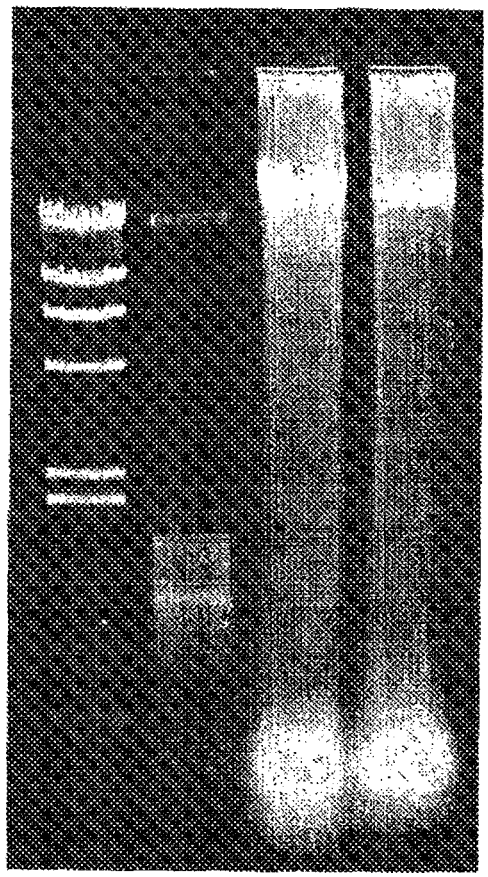
FIG. 2 is a photograph of an ethidium bromide-stained, transilluminated agarose gel showing the results of electrophoresis of nucleic acids from saliva stored in Oragene™

The sample order of FIG. 2 is as follows.

| Lane | Sample | 90° C., 15 min prior to nucleic acid extraction |
| --- | --- | --- |
| 1 | Lambda-HindIII DNA ladder | |
| 2 | RNA marker | |
| 3 | Nucleic acids purified from saliva in Oragene ™ | no |
| 4 | Nucleic acids purified from saliva in Oragene ™ | yes |

Conclusions

This example demonstrates i) the ability of the composition of the present invention to preserve salivary ribonucleic acid for at least 3 days at room temperature and ii) the suitability of the extraction/purification procedure for the recovery of substantially intact ribonucleic acids. This example demonstrates the superiority of the composition of the present invention over Oragene™, in terms of RNA stability.

The preservation and extraction of intact, high molecular weight RNA, indicative of ribosomal RNA (see double bands in lane 7, FIG. 1), suggests that other forms of RNA (such as messenger RNA present in amounts too low to be detected by ethidium bromide staining and transillumination), are also maintained in an intact form in samples collected in the composition of the present invention.

Example 3: Optimizing pH Range for Maintaining the Stability of Pure RNA Derived from Sputum/Saliva Methods Pure RNA was diluted 6-fold into solutions buffered over a wide range of pH values (pH 3.0, 5.0, 6.0, 7.0, 8.2 and 10.0). Following a 16 hour period of incubation at 50° C., to allow partial hydrolysis of the phosphodiester backbone of the RNA to occur, an aliquot of the RNA buffered to each pH value (noted below) was analyzed by electrophoresis on a 0.9% agarose gel and stained with ethidium bromide (FIG. 3).

Figure 3:
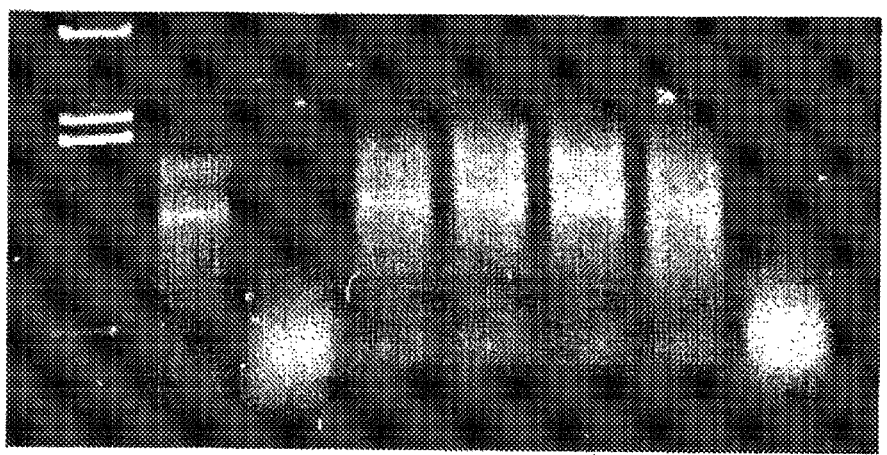
FIG. 3 is a photograph of an ethidium bromide-stained, transilluminated agarose gel showing the results of electrophoresis of RNA samples stored in compositions having a range of pH's.

The sample order of FIG. 3 is as follows:

| Lane | Sample |
| --- | --- |
| 1 | Lambda DNA HindIII digest |
| 2 | RNA marker |
| 3 | RNA, pH 3.0 |
| 4 | RNA, pH 5.0 |
| 5 | RNA, pH 6.0 |
| 6 | RNA, pH 7.0 |
| 7 | RNA, pH 8.2 |
| 8 | RNA, pH 10.0 |

Conclusions

RNA is stable chemically at neutral to slightly acid pH, as indicated by the preservation of the stained double bands characteristic of ribosomal RNA seen in treatments at pH 5.0-8.2. Note that a decrease in intensity of the upper band is expected before a decrease in the lower band. While not wishing to be bound by theory, this is likely due to larger species of ribosomal RNA having a higher probability of suffering one phosphodiester backbone cleavage compared to the shorter RNA species (lower band). The characteristic banding pattern of the 2 ribosomal RNA species disappears entirely at more extreme acid and basic pH values of 3.0 and 10.0, respectively.

Example 4: Demonstration of Potent Rnase Activity in the Cell-Free Fraction of Saliva Methods Three subjects spit one milliliter of saliva into tubes containing an equal volume of saline. Immediately thereafter, the saliva samples and saline were mixed and subjected to a high speed centrifugation to pellet the cells contained within the saliva. The resultant supernatant or cell-free saliva fraction (CFSF) was diluted and then mixed in increasing amounts with a fixed amount (1.0 µg) of pure RNA. The pure RNA mixed with CFSF was incubated at 37° C. for 30 min and then analyzed by agarose gel (1.0%) electrophoresis. The gel was stained with ethidium bromide to visualize the integrity of the RNA (FIG. 4).

Figure 4A:
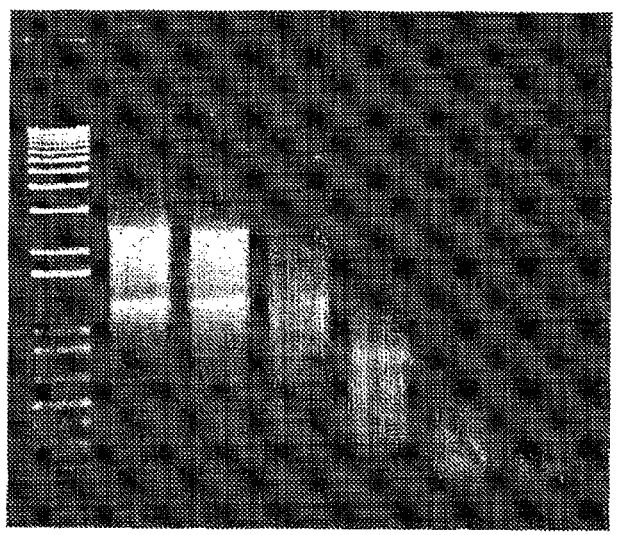
FIG. 4A-C are photographs of ethidium bromide-stained, transilluminated agarose gels showing the results of electrophoresis of RNA combined with a cell-free fraction of saliva; subject 1 (FIG. 4A), subject 2 (FIG. 4B), and subject 3 (FIG. 4C)
Figure 4B:
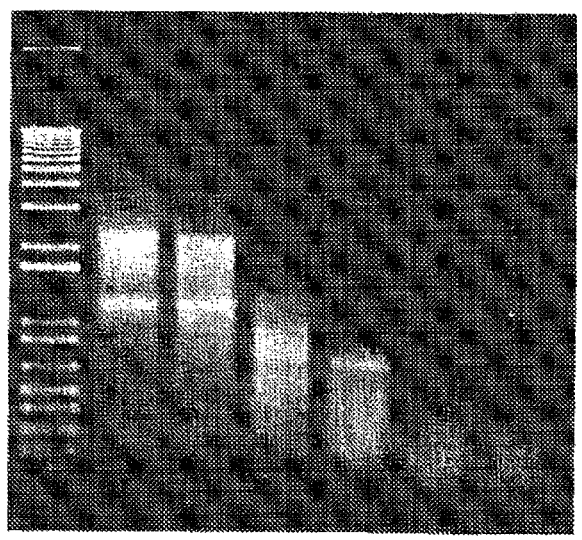
Figure 4C:
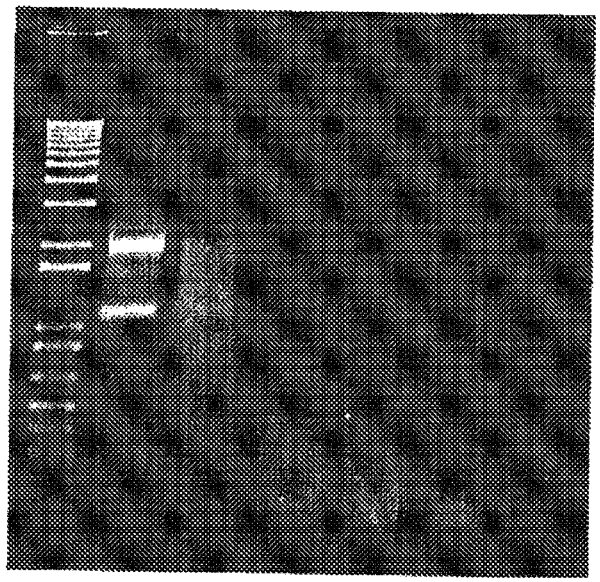

The sample order of FIG. 4 is as follows:

| Lane | Sample |
| --- | --- |
| 1 | 1 Kb+ DNA ladder |
| 2 | Pure RNA + no CFSF |
| 3 | Pure RNA + 0.01 µL CFSF |
| 4 | Pure RNA + 0.05 µL CFSF |
| 5 | Pure RNA + 0.1 µL CFSF |
| 6 | Pure RNA + 0.5 µL CFSF |
| 7 | Pure RNA + 1.0 µL CFSF |

Conclusions

RNA is rapidly degraded when incubated with a fraction of a microliter of cell-free saliva. Hence, potent ribonuclease activity exists in the extracellular fraction of saliva.

This example also demonstrates the existence of considerable variability in salivary ribonuclease among between subjects. Compared to subjects 1 and 2, a much smaller volume of CFSF from subject 3 was required to degrade an equal amount of RNA.

Example 5: Optimal pH for Salivary Ribonuclease Activity

Methods

Figure 5:
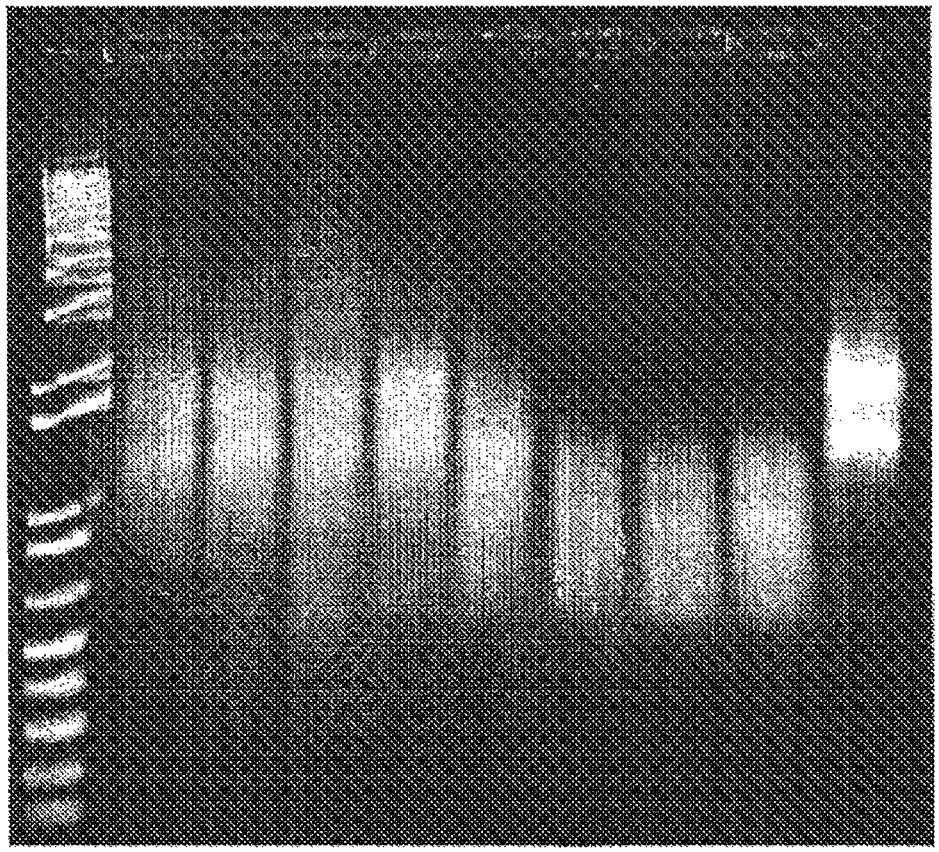
FIG. 5 is a photograph of an ethidium bromide-stained, transilluminated agarose gel showing the results of electrophoresis of RNA combined with a cell-free fraction of saliva over a range of pH's.

To determine the pH range where salivary ribonuclease exhibits activity, an equivalent of 0.1 µL CFSF (Subject 2, example 4) was mixed with 1 µg of pure RNA buffered to pH 5.1, 5.5, 6.0, 6.5, 7.0, 7.5, 8.1 and 8.6. Pure RNA, in the absence of CFSF (lane 10), was included in this example to illustrate the state or intact nature of the RNA utilized in this example. Following incubation at 37° C. for 30 min, the samples were analyzed by agarose gel (0.9%) electrophoresis and stained with ethidium bromide (FIG. 5). Indications of RNA degradation include 1) the disappearance of one or both ribosomal RNA subunits, the distinct double bands at the mid-point of the gel, 2) the appearance of an elongated smear of ethidium bromide-stained material, and/or 3) the hastened mobility of ethidium bromide-stained material on the gel with respect to the control RNA marker.

The sample order of FIG. 5 is as follows:

| Lane | Sample |
|------|--------|
| 1 | 1 Kb+ DNA ladder |
| 2 | Pure RNA + CFSF, pH 5.1 |
| 3 | Pure RNA + CFSF, pH 5.5 |
| 4 | Pure RNA + CFSF, pH 6.0 |
| 5 | Pure RNA + CFSF, pH 6.5 |
| 6 | Pure RNA + CFSF, pH 7.0 |
| 7 | Pure RNA + CFSF, pH 7.5 |
| 8 | Pure RNA + CFSF, pH 8.1 |
| 9 | Pure RNA + CFSF, pH 8.6 |
| 10 | Pure RNA + no CFSF |

Conclusions

Pure RNA, buffered at pH>6.5, was rapidly degraded (lanes 6-9) upon the addition of 0.1 µL of cell-free saliva. Between pH 5.1 and 6.5, pure RNA remained intact in the presence of cell-free saliva. These findings suggest that ribonuclease endogenous to saliva displays optimal enzymatic activity at neutral (pH 7.0) to slightly alkaline pH. There was no significant ribonuclease activity detected in acid conditions (lanes 2-5).

Example 6: Stability of RNA Over a Range of SDS Concentration

Methods

Figure 6:
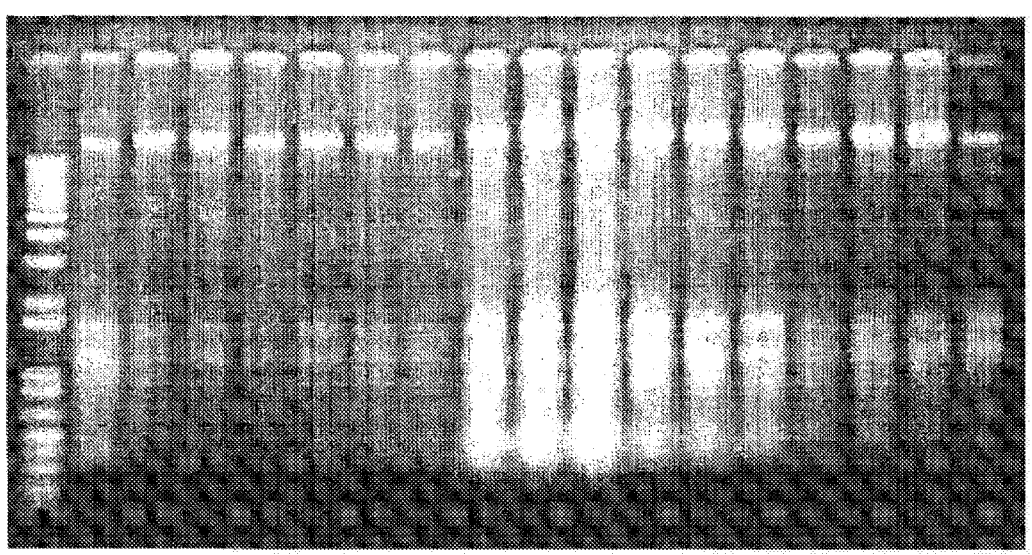
FIG. 6 is photograph of an ethidium bromide-stained, transilluminated agarose gel showing the results of electrophoresis of RNA in saliva stored in a composition of the present invention over a range of SDS concentrations.

Examples of RNA extracted from saliva taken from 5 subjects into one of 3 compositions of the present invention are shown (FIG. 6). Saliva was collected and immediately mixed with an equal volume of the indicated composition. The compositions contained SDS (sodium dodecyl sulphate, at the concentration indicated in the table below) and were buffered at pH 6.2 with 50 mM CDTA (sodium salt of cyclohexane diaminetetraacetic acid). Each sample of saliva was mixed with an equal volume of the indicated composition and stored for 3 weeks at room temperature. To examine the RNA contained in each sample, a 50 µl aliquot was removed and heated at 90° C. for 15 min, then diluted 5-fold. Proteinase K was added to each diluted aliquot and then incubated at 50° C. for 1 hour to allow the protease to digest proteins. After cooling to room temperature, 10 µl of a 2.5 M solution of KCl was added to precipitate the SDS; the sample was then centrifuged to remove the precipitated SDS. Cold 95% ethanol (2 volumes) was added to the clear supernatant to precipitate the nucleic acids. After standing for 1 hour at −20° C., the precipitated nucleic acids were dissolved in 25 µl of a dilute buffer. 10 µl of this solution (equivalent to about 10 µl of the original saliva) was applied to a 0.9% agarose gel and subjected to electrophoresis for 1 hour. The gel was stained with ethidium bromide and photographed under transillumination. In each sample lane, the upper band is genomic DNA. The 2 bands in the middle of the gel represent ribosomal RNA that was present in saliva and preserved by the indicated compositions.

The sample order of FIG. 6 is as follows:

| Lane | Sample | Amount of SDS in composition (%) |
|------|--------|----------------------------------|
| 1 | 1 Kb+ DNA ladder | |
| 2 | RNA marker | |
| 3 | Subject 1 | 16 |
| 4 | Subject 1 | 12 |
| 5 | Subject 1 | 8 |
| 6 | Subject 2 | 16 |
| 7 | Subject 2 | 12 |
| 8 | Subject 2 | 8 |
| 9 | Subject 3 | 16 |
| 10 | Subject 3 | 12 |
| 11 | Subject 3 | 8 |
| 12 | Subject 4 | 16 |
| 13 | Subject 4 | 12 |
| 14 | Subject 4 | 8 |
| 15 | Subject 5 | 16 |
| 16 | Subject 5 | 12 |
| 17 | Subject 5 | 8 |
| 18 | RNA marker | |

Conclusions

These data demonstrate that RNA in saliva is stable for at least 3 weeks at room temperature when mixed 1:1 with compositions including a range of anionic detergent concentrations (8-16% SDS), buffered to a slightly acidic pH (6.2). These data also illustrate considerable variability between subjects in the amount of RNA present in saliva.

Example 7: Stability of RNA in Saliva Using the Composition of the Present Invention at Room Temperature and 37° C.

In this example, the composition comprised 16% SDS, 50 mM CDTA, buffered at pH 6.2. Saliva samples were mixed 1:1 with the composition and stored for 7 days at either room temperature (RT) or 37° C. Incubating samples at 37° C., compared to RT, is expected to accelerate the degradation of RNA by salivary ribonuclease, if present, should it retain activity in the composition of the present invention. The samples were heated at 90° C. for 15 min, then diluted 5-fold and incubated at 50° C. for 1 hour with proteinase K. SDS was precipitated with potassium chloride and, after the precipitate was removed by centrifugation, nucleic acids were precipitated from the supernatant with 2 volumes of cold 95% ethanol. A portion of each precipitated nucleic acid sample was analyzed by agarose gel electrophoresis, stained with ethidium bromide and photographed under transillumination (FIG. 7).

Figure 7:
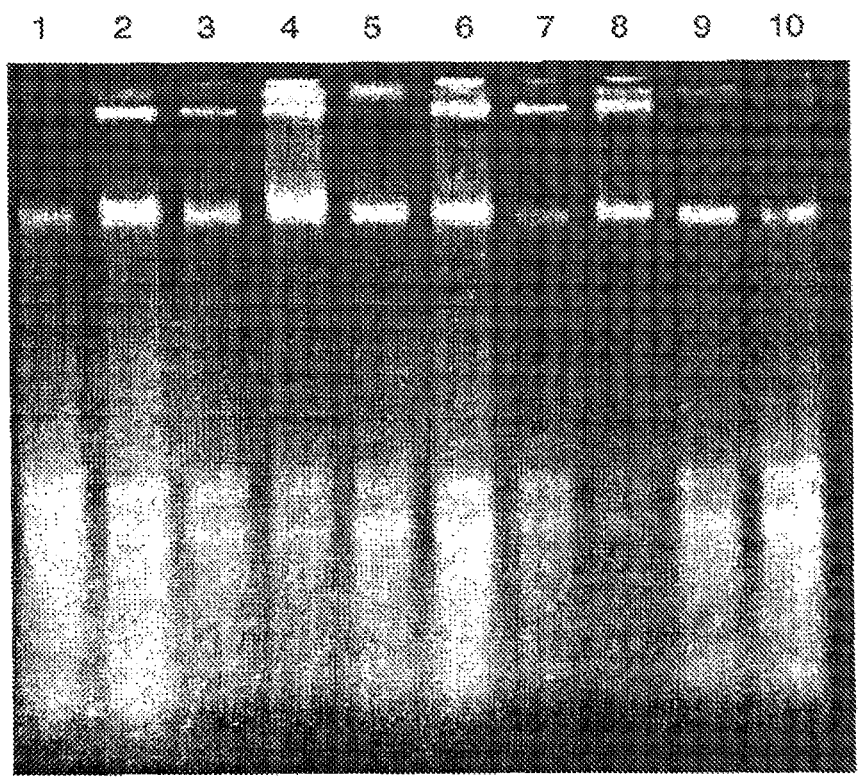
FIG. 7 is a photograph of an ethidium bromide-stained, transilluminated agarose gel showing the results of electrophoresis of RNA in saliva when stored at room temperature compared to 37° C., using a composition of the present invention.

The sample order of FIG. 7 is as follows:

| Lane | Sample |
|---|---|
| 1 | RNA marker |
| 2 | Subject 1-RT |
| 3 | Subject 2-RT |
| 4 | Subject 3-RT |
| 5 | Subject 4-RT |
| 6 | Subject 1-37° C. |
| 7 | Subject 2-37° C. |
| 8 | Subject 3-37° C. |
| 9 | Subject 4-37° C. |
| 10 | RNA marker |

Conclusions

This example demonstrates the efficacy of the composition of the present invention for stabilizing RNA in samples of saliva. After 1 week at 37° C., saliva samples from 4 subjects showed no appreciable degradation of high molecular weight RNA.

Example 8: Testing a RNA-Stabilizing Composition Containing a Different Buffer

Figure 8:
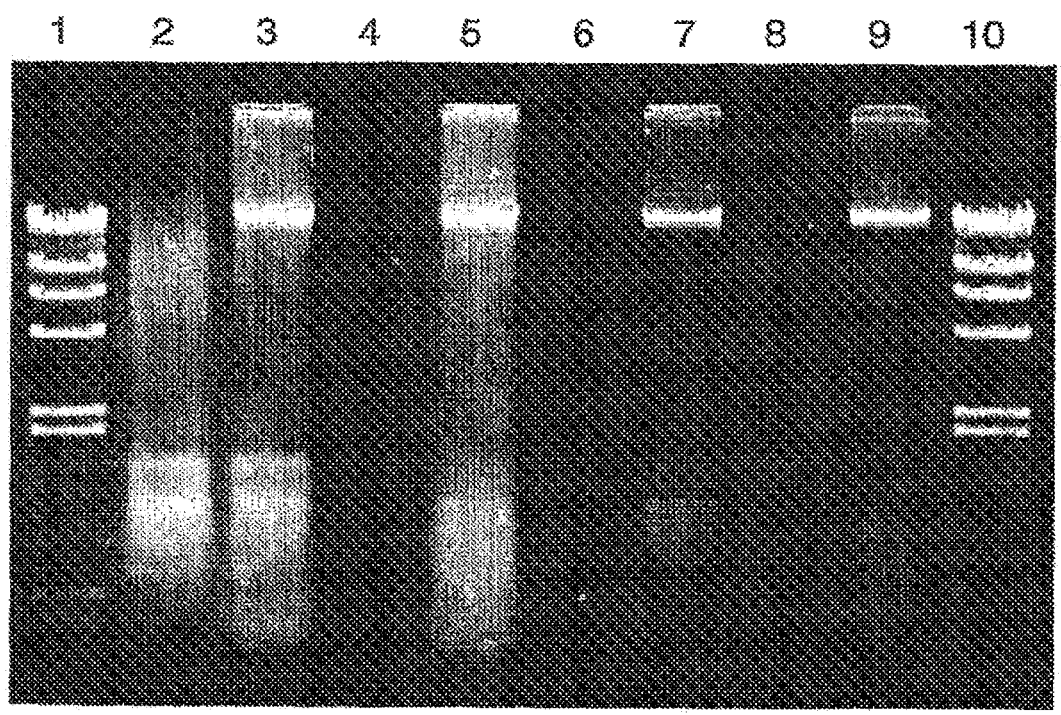
FIG. 8 is a photograph of an ethidium bromide-stained, transilluminated agarose gel showing the results of electrophoresis of RNA in saliva stored at room temperature in a composition of the present invention.

In this example, sodium citrate/citric acid buffer ($pK_a$ 6.4, 50 mM) was substituted for CDTA, which was used to buffer the pH in previous compositions. As in other examples, saliva was collected from two subjects and mixed 1:1 with the composition (4% SDS, 50 mM citric acid buffered to pH 6.6). Samples were then stored at room temperature for 3 weeks. To extract RNA present in the saliva/composition mixture, the samples were incubated at 50° C. for 1 hour with proteinase K, heated at 90° C. for 15 min, SDS was precipitated with potassium chloride and, after the precipitate was removed by centrifugation, nucleic acids were precipitated from the supernatant with 2 volumes of cold ethanol. To confirm the extracted material was RNA, a portion of the precipitated nucleic acids was treated with pancreatic ribonuclease (RNase). RNase-treated and -untreated extracts were then resolved by agarose gel electrophoresis and stained with ethidium bromide as before (FIG. 8). Note that part of the rapidly migrating, RNase-resistant material in lanes 5 and 9 is likely DNA, which has been denatured and partially degraded by the period of heating at 90° C.

The sample order of FIG. 8 is as follows:

| Lane | Sample |
|---|---|
| 1 | Lambda DNA HindIII digest |
| 2 | RNA marker |
| 3 | Subject 1 |
| 4 | Blank lane |
| 5 | Subject 1 + RNase |
| 6 | Blank lane |
| 7 | Subject 2 |
| 8 | Blank lane |
| 9 | Subject 2 + RNase |
| 10 | Lambda DNA HindIII digest |

Conclusions

This example demonstrates the suitability of substituting citric acid for CDTA to buffer the pH of the composition.

Example 9: Testing the RNA-Stabilizing Solution Using a Different Anionic Detergent In this example, Sarkosyl (N-Lauroylsarcosine sodium salt or sodium lauroyl sarcosinate) was substituted for SDS. Saliva was collected from 3 subjects and mixed 1:1 with two compositions, i) 4% Sarkosyl, 50 mM CDTA buffered to pH 6.6 and ii) 8% Sarkosyl, 50 mM CDTA buffered to pH 6.6. Samples were then stored at room temperature for 3 weeks. To extract RNA present in the saliva/composition mixture, a portion of the samples were incubated at 50° C. for 1 hour with proteinase K, heated at 90° C. for 15 min, treated with potassium chloride and centrifuged. Nucleic acids remaining in the supernatant were precipitated with 2 volumes of cold ethanol. To confirm the extracted material was RNA, a portion of the precipitated nucleic acids was treated with pancreatic ribonuclease (RNase). RNase-treated and -untreated extracts were then resolved by agarose gel electrophoresis and stained with ethidium bromide (FIG. 9).

Figure 9:
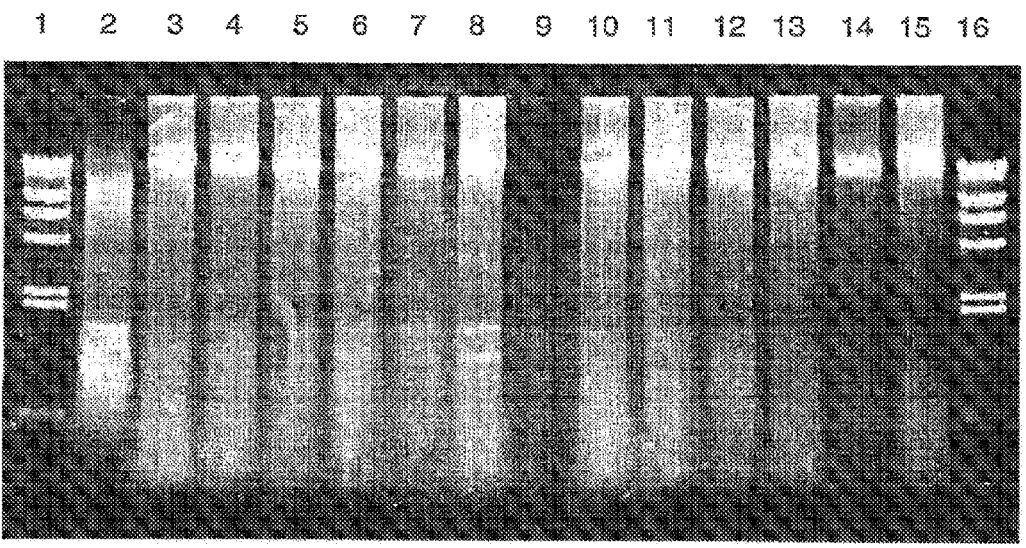
FIG. 9 is a photograph of an ethidium bromide-stained, transilluminated agarose gel showing the results of electrophoresis of RNA in saliva stored at room temperature in a composition of the present invention.

The sample order of FIG. 9 is as follows:

| Lane | Sample |
|---|---|
| 1 | Lambda DNA HindIII digest |
| 2 | RNA marker |
| 3 | Subject 1, 4% Sark |
| 4 | Subject 1, 8% Sark |
| 5 | Subject 2, 4% Sark |
| 6 | Subject 2, 8% Sark |
| 7 | Subject 3, 4% Sark |
| 8 | Subject 3, 8% Sark |
| 9 | Blank lane |
| 10 | Subject 1, 4% Sark + RNase |
| 11 | Subject 1, 8% Sark + RNase |
| 12 | Subject 2, 4% Sark + RNase |
| 13 | Subject 2, 8% Sark + RNase |
| 14 | Subject 3, 4% Sark + RNase |
| 15 | Subject 3, 8% Sark + RNase |
| 16 | Lambda DNA HindIII digest |

Conclusions

This experiment shows that Sarkosyl, another strong anionic detergent, can be substituted for SDS in the composition of the present invention. Examples 6 and 0.9 demonstrate that anionic detergents, with appropriate buffering agents, effectively stabilize RNA in saliva.

Example 10: Demonstration that a Step Involving Brief Heating Above 50° C. is Beneficial in the Extraction of RNA from Saliva In this example, the composition comprised 4% SDS, 50 mM CDTA, buffered at pH 6.6. Saliva sample from one subject was mixed 1:1 with the composition and incubated for 6 days at room temperature. To extract RNA present in the saliva/composition mixture, the samples were first incubated at 50° C. for 1 hour with proteinase K to digest protein. Aliquots were taken and heated for 15 minutes at 50° C., 55° C., 60° C., 65° C., 70° C., 75° C., 80° C., 85° C. or 90° C. SDS was precipitated from heated aliquots with potassium chloride and, after the precipitate was removed by centrifugation, nucleic acids were precipitated from the supernatant with 2 volumes of cold ethanol. A portion of each precipitated nucleic acid sample was analyzed by agarose gel electrophoresis, stained with ethidium bromide and photographed under transillumination (FIG. 10).

Figure 10:
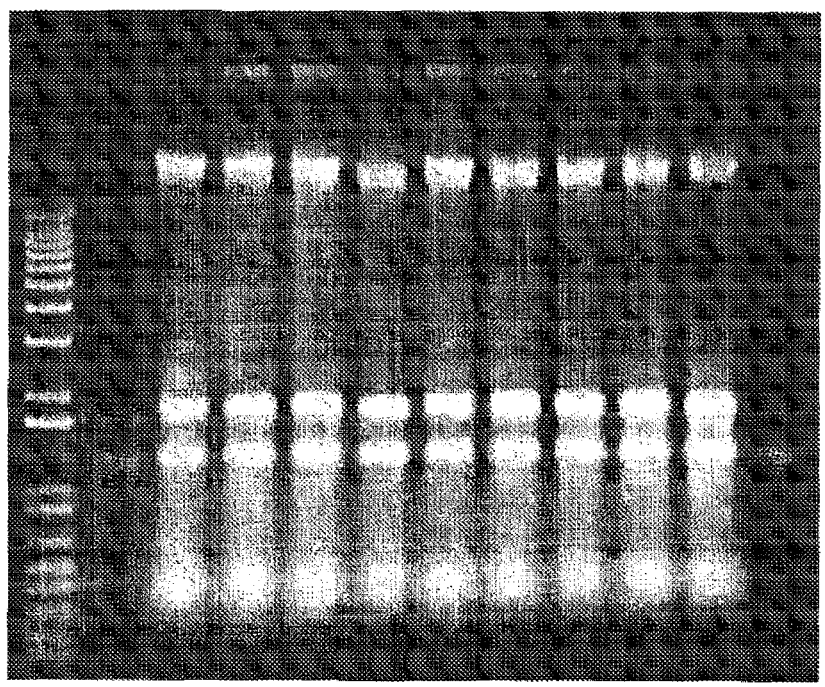
FIG. 10 is a photograph of an ethidium bromide-stained, transilluminated agarose gel showing the results of electrophoresis of RNA samples stored in compositions of the present invention and heated at various temperatures subsequent to storage at room temperature.

The sample order of FIG. 10 is as follows:

| Lane | Sample |
|---|---|
| 1 | 1 Kb⁺ DNA ladder |
| 2 | RNA marker |

-continued

| Lane | Sample |
|------|--------|
| 3 | 50° C. |
| 4 | 55° C. |
| 5 | 60° C. |
| 6 | 65° C. |
| 7 | 70° C. |
| 8 | 75° C. |
| 9 | 80° C. |
| 10 | 85° C. |
| 11 | 90° C. |
| 12 | RNA marker |

Conclusions

In this example, 15 minutes of heating at temperatures above 50° C. and as high as 90° C. improved the yield of high molecular weight RNA extracted from this saliva/composition sample, compared to 50° C. alone. These results also show that the extracted RNA is not significantly degraded by a 15 minute heating step at temperatures up to 90° C.

Example 11: Demonstration that a Step Involving Brief Heating at 90° C. is Beneficial in the Extraction of RNA from Saliva In this example, the composition comprised 4% SDS, 50 mM CDTA, buffered at pH 6.6. Saliva samples from 2 subjects were mixed 1:1 with the composition and incubated for 4 days at room temperature. To extract RNA present in the saliva/composition mixture, the samples were first incubated at 50° C. for 1 hour with proteinase K to digest protein. Aliquots were taken and heated at 90° C. for 0, 5, 15, 30 or 60 min, then diluted 4-fold with water and incubated for an additional 18 hours at room temperature. Dilution of the sample permitted testing the efficiency of the heating step by decreasing the concentration of SDS to a level that would normally permit RNase activity. SDS was precipitated with potassium chloride and, after the precipitate was removed by centrifugation, nucleic acids were precipitated from the supernatant with 2 volumes of cold ethanol. A portion of each precipitated nucleic acid sample was analyzed by agarose gel electrophoresis, stained with ethidium bromide and photographed under transillumination FIG. 11; subject 1, left panel; subject 2, right panel).

The sample order of FIG. 11 is as follows:

| Lane | Time (min) at 90° C. |
|------|----------------------|
| 1 | 0 |
| 2 | 5 |
| 3 | 15 |
| 4 | 30 |
| 5 | 60 |
| 6 | RNA marker |

Conclusions

In this example, 5-15 minutes of heating at 90° C. improved the yield of intact RNA extracted from 2 subjects' samples, compared to unheated samples. Evidence of RNA degradation was observed in samples heated at 90° C. for 30 and 60 minutes.

Additionally, the recovery of substantially intact ribosomal RNA following heating, dilution and then further incubation of samples, suggests that the composition of the present invention and the extraction protocol result in purified material with diminished ribonuclease activity.

Example 12: Human mRNA is Extracted and Purified from Samples Collected in the Present Composition In this example, it is demonstrated that Reverse Transcriptase-Polymerase Chain Reaction (RT-PCR) can be used to detect human-specific messenger RNA in RNA recovered from the saliva of six subjects collected in the composition of the present invention.

Methods

Saliva samples from 6 subjects were mixed 1:1 with the composition (4% SDS, 50 mM CDTA, buffered at pH 6.6) and stored for 10-16 days at room temperature. Following storage at room temperature, a portion of each saliva/composition mixture was heated at 50° C. for 1 hour with proteinase K, followed by 90° C. for 15 min. SDS was precipitated with potassium chloride and, after the precipitate was removed by centrifugation, nucleic acids were precipitated from the supernatant with 2 volumes of cold 95% ethanol. A portion of each precipitated nucleic acid sample was analyzed by agarose gel electrophoresis, stained with ethidium bromide and photographed under transillumination (FIG. 12).

Figure 12:
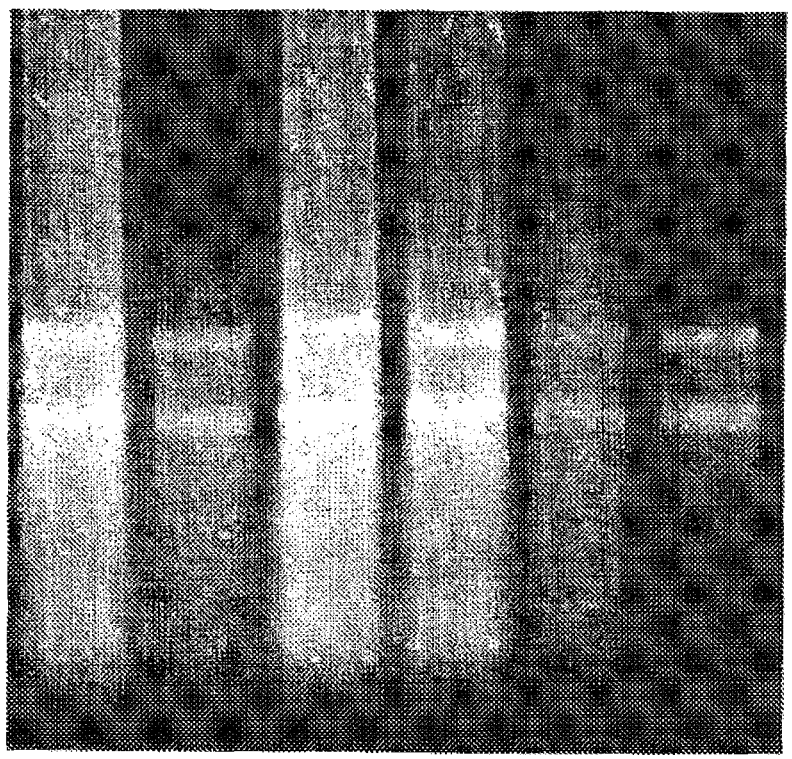
FIG. 12 is a photograph of an ethidium bromide-stained, transilluminated agarose gel showing the results of electrophoresis of RNA samples stored at room temperature for 1016 days at room temperature in a composition of the present invention.

A modified version of the Schmidt-Tannhauser procedure was used to estimate the total amount of RNA in the saliva samples collected from the same 6 subjects in the composition of the present invention (FIG. 12). In brief, a portion of each sample was treated with sodium hydroxide to selectively degrade RNA to oligo- or mono-nucleotides (rendering it non-precipitable by cold hydrochloric acid), leaving undegraded DNA precipitable with cold HCl. In this way, DNA and RNA are separated and can be quantified by absorbance measurements at 260 nm.

Figure 13:
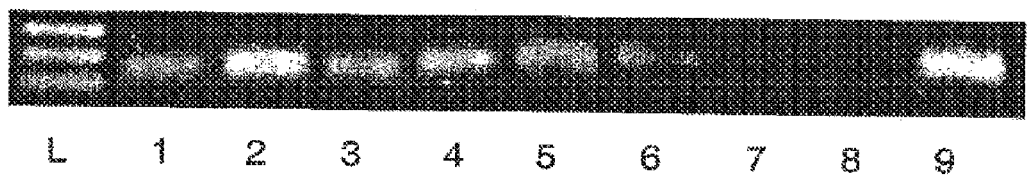
FIG. 13 is a photograph of an ethidium bromide-stained, transilluminated agarose gel showing the results of electrophoresis of RT-PCR products.
Figure 15:
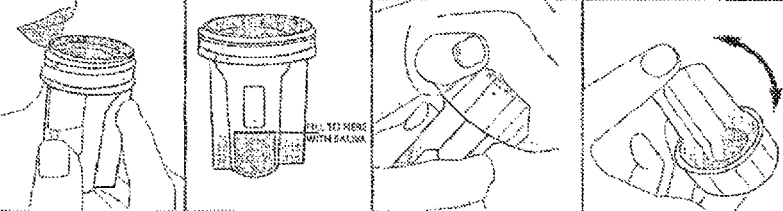
FIG. 15 is a diagram depicting steps that may be followed to collect saliva from a subject.

To demonstrate that human messenger RNA (mRNA) is stabilized and recovered from these saliva samples, a portion of purified sample from each subject served as template in RT-PCR analysis using human-specific primers for β2-microglobulin messenger RNA (FIG. 13). Specifically, a portion of precipitated nucleic acid sample from each subject (FIG. 12) was treated with DNase to digest DNA. The DNA-free sample was then mixed with random hexanucleotide primers and M-MVL reverse transcriptase to synthesize complementary DNA (cDNA). Finally, the cDNA was diluted and mixed with human-specific primers (β2-microglobulin-forward 5' cgctactctctctttctggc and β2-microglobulin-reverse 5' aacttcaatgtcggatggat) and Taq DNA polymerase for conventional PCR (Table I); SybrGreen was added for quantitative real-time PCR analysis (Table II). The Ct value, as shown in FIG. 15, is inversely proportional to the amount of messenger RNA in the sample. RNA purified from a human colon carcinoma cell line, HCT-116, served as a positive control for RT-PCR analysis. Negative controls include reactions in which no M-MVL RT or cDNA was added.

TABLE I

| Subject | Estimated amount (µg) of RNA in total sample |
|---------|----------------------------------------------|
| 1 | 99.8 |
| 2 | 43.6 |
| 3 | 337.5 |
| 4 | 330.5 |

TABLE I-continued

| Subject | Estimated amount (µg) of RNA in total sample |
|---|---|
| 5 | 96.8 |
| 6 | 96.8 |

The sample order of FIG. 13 is as follows:

| Lane | Source of RNA for RT-PCR with primers specific for human β2-microglobulin (140 bp) |
|---|---|
| L | 1 Kb+ DNA ladder |
| 1 | Subject 1 |
| 2 | Subject 2 |
| 3 | Subject 3 |
| 4 | Subject 4 |
| 5 | Subject 5 |
| 6 | Subject 6 |
| 7 | No RT Negative control |
| 8 | No template (cDNA): Negative control |
| 9 | HCT116 cell line: Positive control |

TABLE II

Real time-PCR with primers specific for human β2-microglobulin.

| Sample | Ct value |
|---|---|
| Subject 1 | 26.06 |
| Subject 2 | 20.72 |
| Subject 3 | 23.62 |
| Subject 4 | 23.9 |
| Subject 5 | 24.55 |
| Subject 6 | 29.56 |
| No RT | >40 |
| HCT116 cell line: Positive control | 20.24 |
| No template (cDNA): Negative control | >40 |

Conclusions

This example demonstrates that human messenger RNA in saliva is stabilized by the composition of the present invention and the extracted material is suitable for RT-PCR analysis.

Example 13: Preservation, Release and Purification of Viral RNA Mixed with Saliva Collected in the Composition of the Present Invention In this example, it is demonstrated that Reverse Transcriptase-Polymerase Chain Reaction (RT-PCR) can be used to detect viral RNA in total RNA recovered from saliva collected in the composition of the present invention.

Methods

Two saliva (1 mL) samples from subject 1 were 'spiked' with $4.25 \times 10^9$ pfu (plaque-forming units) of Vesicular Stomatitis Virus (VSV) and incubated at room temperature for 5 min prior to being mixed 1:1 with 4% SDS, 50 mM CDTA, buffered at pH 6.6. A 0.5 mL aliquot from each saliva/composition sample was removed and heated at 50° C. for 1 hr with proteinase K, followed by 90° C. for 15 min. SDS was precipitated with potassium chloride and, after the precipitate was removed by centrifugation, nucleic acids were precipitated from the supernatant with 2 volumes of cold 95% ethanol. Each precipitate was re-dissolved in an appropriate buffer (100 µl of CBS containing 0.1 M NaCl) and then nucleic acids were re-precipitated by adding 200 µl of cold ethanol and incubating for 40 min at −20° C. Precipitated nucleic acids were re-dissolved in 50 µl of water with ribonuclease inhibitor. One sample from subject 1 was kept at room temperature for 4 weeks prior to purifying the nucleic acids as described above. A 2 mL saliva sample from subject 2 was mixed 1:1 with the composition of the present invention, then spiked with $5.0 \times 10^7$ pfu of VSV. After incubation at room temperature for 18 hours, RNA was extracted from a 0.5 mL aliquot by incubating at 80° C. for 40 min; subsequent steps in purification were as described above.

To demonstrate that viral RNA is stabilized and can be recovered from these saliva samples, a portion of the purified nucleic acids was used as template in RT-PCR, primed with random hexanucleotide. Specifically, a portion of the sample was mixed with random hexanucleotide primers and M-MVL reverse transcriptase to synthesize complementary DNA (cDNA). A portion of the cDNA was mixed with virus-specific primers (VSV-forward 5' ggattattccctctgcc and VSV-reverse 5' gttcccttctgtggtag), Taq DNA polymerase and SybrGreen and analysed by quantitative real-time PCR analysis. The Ct value, as shown in FIGS. 16-18, is inversely proportional to the amount of virus template RNA in the sample. Plasmid DNA encoding the virus sequences (pVSV) served as a positive control for RT-PCR analysis. Negative controls include reactions in which no M-MVL RT (-RT) or no cDNA was added. RT-PCR results are shown for three separate experiments (Tables III-V).

TABLE III

| Sample/Source of viral RNA | Ct value | Viral particles added (assuming 100% efficiency in stability, extraction and cDNA synthesis) |
|---|---|---|
| pVSV | 11.3 | 15 ng plasmid DNA |
| pVSV | 17.2 | 3 ng plasmid DNA |
| NTC (no template control) | 39.9 | |
| VSV in composition with poly(A) RNA carrier | 19.4 | $2.81 \times 10^9$ pfu |
| VSV in saliva/composition (subject 1, sample 1) after 1 day at room temperature | 29.8 | $1.48 \times 10^8$ pfu |
| VSV in saliva/composition (subject 1, sample 2) | 29.5 | $1.48 \times 10^8$ pfu |
| VSV in saliva/composition (subject 1, sample 1) after 4 weeks at room temperature | 25.4 | $1.06 \times 10^9$ pfu |
| VSV in saliva/composition (subject 2) after 1 day at room temperature | 29.8 | $1.25 \times 10^6$ pfu |
| -RT using VSV in saliva/composition (subject 2) after 1 day at room temperature | >40.0 | $1.25 \times 10^6$ pfu |

TABLE IV

| Sample/Source of viral RNA | Ct value | Viral particles added (assuming 100% efficiency in stability, extraction and cDNA synthesis) |
|---|---|---|
| pVSV | 13.0 | 15 ng plasmid DNA |
| NTC | >45.0 | |
| VSV in composition with polyA RNA carrier | 15.4 | $2.81 \times 10^9$ pfu |
| VSV in saliva/composition (subject 1) after 4 weeks at room temperature | 27.5 | $1.06 \times 10^9$ pfu |

TABLE IV-continued

| Sample/Source of viral RNA | Ct value | Viral particles added (assuming 100% efficiency in stability, extraction and cDNA synthesis) |
|---|---|---|
| VSV in saliva/composition (subject 2) after 1 day at room temperature | 30.5 | $1.25 \times 10^6$ pfu |
| −RT using VSV in saliva/composition (subject 2) after 1 day at room temperature | 40.4 | $1.25 \times 10^6$ pfu |

TABLE V

| Sample/Source of viral RNA | Ct value | Viral particles added (assuming 100% efficiency in stability, extraction and cDNA synthesis) |
|---|---|---|
| pVSV | 16.6 | 15 ng plasmid DNA |
| NTC | 39.3 | |
| VSV in composition containing polyA RNA carrier | 19.3 | $2.81 \times 10^9$ pfu |
| VSV in saliva/composition (subject 1, sample 1) after 1 day at room temperature | 26.4 | $1.48 \times 10^8$ pfu |
| VSV in saliva/composition (subject 1, sample 1) after 4 weeks at room temperature | 32.1 | $1.06 \times 10^9$ pfu |
| VSV in composition alone with LPA (linear polyacrylimide) | 33.0 | $4.25 \times 10^9$ pfu |
| VSV in Oragene alone with LPA | 39.4 | $4.25 \times 10^9$ pfu |
| −RT using VSV in composition containing polyA RNA carrier | 36.6 | $4.25 \times 10^9$ pfu |

Conclusions

This example demonstrates that viral RNA in saliva is stabilized by the composition of the present invention and the extracted material is suitable for RT-PCR analysis.

Example 14: Stability of RNA in Saliva at Room Temperature for 8 Weeks

Figure 14A:
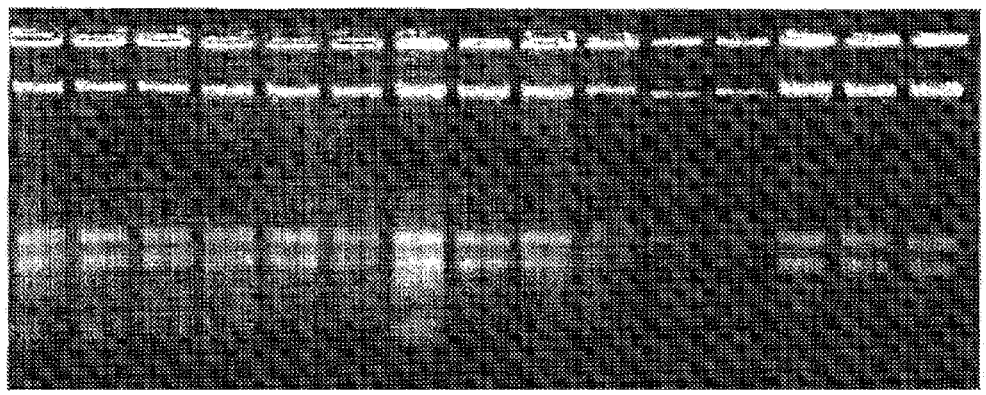
FIG. 14A-D are photographs of ethidium bromide-stained, transilluminated agarose gels showing the results of electrophoresis of RNA samples from saliva stored at the indicated temperature for 1 week (FIG. A-B) and 8 weeks (FIG. C-D)
Figure 14B:
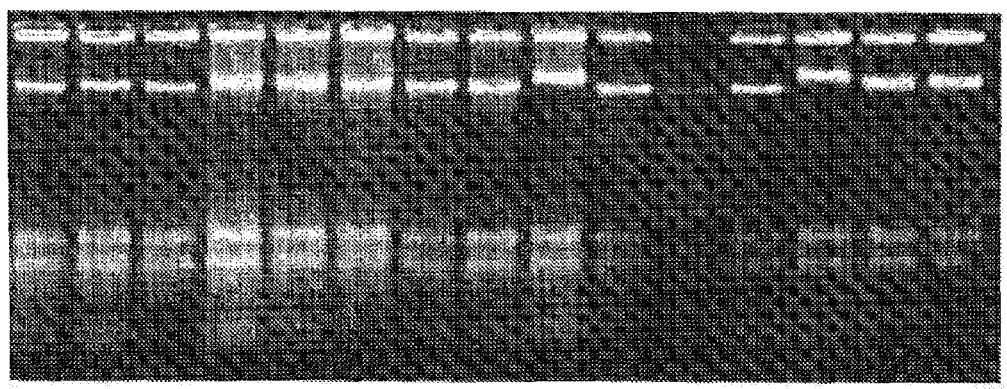
Figure 14C:
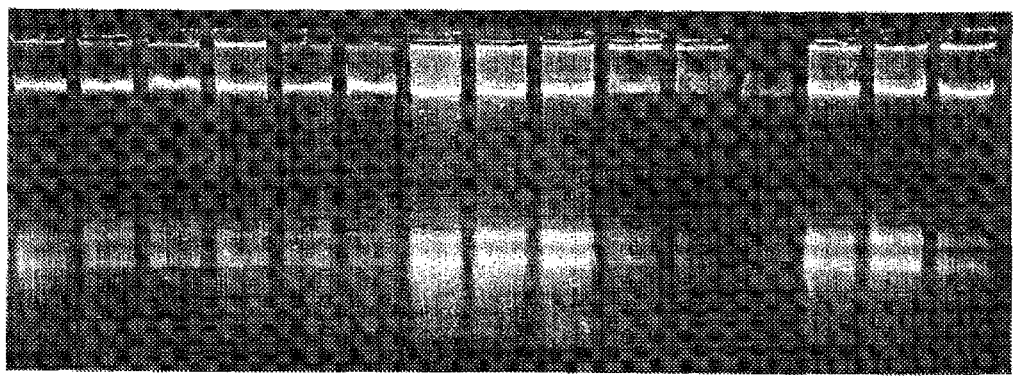
Figure 14D:
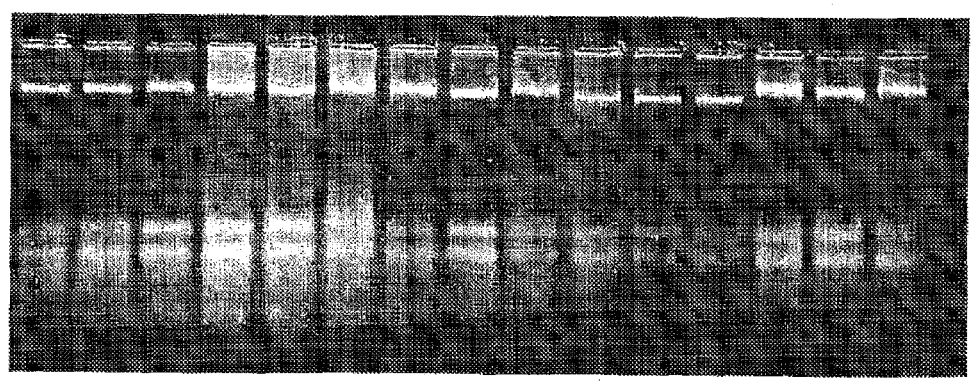

In this example, the composition comprised 4% SDS, 50 mM LiCDTA, 250 mM LiCl, adjusted to pH 6.8. Saliva samples (2 mL) from 10 subjects were collected and mixed 1:1 with the composition. Immediately after collection, the samples were vigorously shaken and 100 μL aliquots were removed. Individual aliquots were stored at room temperature (RT), 4° C., and −20° C. Following 1 week and 8 weeks storage at RT, 4° C., and −20° C., the samples were analysed. To extract RNA from the saliva/composition mixture, the aliquots were heated at 50° C. for 1 hour in the presence of proteinase K, then at 90° C. for 15 min. SDS was precipitated with potassium chloride and, after the precipitate was removed by centrifugation, nucleic acids were precipitated from the supernatant with 2 volumes of cold 95% ethanol. A portion of each precipitated nucleic acid sample was analyzed by agarose gel electrophoresis, stained with ethidium bromide and photographed under transillumination (FIGS. 14A and 14B).

To demonstrate that human messenger RNA (mRNA) is stabilized and can be recovered from these saliva samples after 1 and 8 weeks at room temperature, a portion of purified sample from each subject was used as template in Reverse Transcriptase-PCR (RT-PCR) analysis using primers specific for human 18S ribosomal RNA. Specifically, a portion of precipitated nucleic acid sample from each subject was treated with DNase to remove DNA prior to the Reverse Transcriptase step. The DNA-free sample was then mixed with random hexanucleotide primers and M-MVL reverse transcriptase to synthesize complementary DNA (cDNA). Finally, the cDNA was diluted and mixed with human-specific primers (human 18S-165 forward 5' gtg-gagcgatttgtctggtt and human 18S-165 reverse 5' gga-catctaagggcatcacag), Taq DNA polymerase and SybrGreen for quantitative real-time PCR analysis. The Ct (Crossing Threshold) values, as shown in FIG. 20, are inversely proportional to the amount of 18S RNA in the sample. RNA purified from a human colon carcinoma cell line, HCT-116, served as a positive control for RT-PCR analysis. Negative controls include reactions in which no M-MVL RT (-RT) or no cDNA/template was added.

The sample order of FIG. 14 is as follows:

| Lane | Sample | Storage condition |
|---|---|---|
| 1 | Subject 1 | RT |
| 2 | Subject 1 | 4° C. |
| 3 | Subject 1 | −20° C. |
| 4 | Subject 2 | RT |
| 5 | Subject 2 | 4° C. |
| 6 | Subject 2 | −20° C. |
| 7 | Subject 3 | RT |
| 8 | Subject 3 | 4° C. |
| 9 | Subject 3 | −20° C. |
| 10 | Subject 4 | RT |
| 11 | Subject 4 | 4° C. |
| 12 | Subject 4 | −20° C. |
| 13 | Subject 5 | RT |
| 14 | Subject 5 | 4° C. |
| 15 | Subject 5 | −20° C. |
| 16 | Subject 6 | RT |
| 17 | Subject 6 | 4° C. |
| 18 | Subject 6 | −20° C. |
| 19 | Subject 7 | RT |
| 20 | Subject 7 | 4° C. |
| 21 | Subject 7 | −20° C. |
| 22 | Subject 8 | RT |
| 23 | Subject 8 | 4° C. |
| 24 | Subject 8 | −20° C. |
| 25 | Subject 9 | RT |
| 26 | Subject 9 | 4° C. |
| 27 | Subject 9 | −20° C. |
| 28 | Subject 10 | RT |
| 29 | Subject 10 | 4° C. |
| 30 | Subject 10 | −20° C. |

TABLE VI

Real time-PCR with primers specific for human 18S ribosomal RNA.

| Saliva Sample | 1 week aliquot Ct value | 1 week aliquot −RT Ct value | 8 week aliquot Ct value | 8 week aliquot −RT Ct value |
|---|---|---|---|---|
| Subject 1 | 13.7 | 27.9 | 16.5 | 28.6 |
| Subject 2 | 12.6 | 26.7 | 13.0 | 29.1 |
| Subject 3 | 13.9 | 26.5 | 13.8 | 27.8 |
| Subject 4 | 13.7 | 28.4 | 13.3 | 28.5 |
| Subject 5 | 14.9 | 28.6 | 13.6 | 29.1 |
| Subject 6 | 15.5 | 26.7 | 13.6 | 22.1 |
| Subject 7 | 19.2 | 29.2 | 18.9 | 27.2 |
| Subject 8 | 17.6 | 30.7 | 18.3 | 23.9 |
| Subject 9 | 13.0 | 22.0 | 17.1 | 23.9 |
| Subject 10 | 18.9 | 22.6 | 17.3 | 23.8 |
| HCT116 cell line: Positive control | 10.8 | 30.6 | | |
| No template (no cDNA): Negative control | 30.8 | | | |

Conclusions

These examples demonstrate the efficacy of the composition of the present invention for stabilizing RNA in samples of saliva for prolonged periods of time at room temperature. After 8 weeks, saliva samples from 10 subjects showed no appreciable degradation of high molecular weight RNA (as shown in FIGS. 14A and 14B) and no significant change in the Ct value for human 18S ribosomal RNA (as shown in Table VI).

Example 15: Extraction and Purification of Human RNA from Infants and Young Children In this example, it is demonstrated that RT-PCR can be used to detect human-specific messenger RNA in RNA recovered from the saliva of 11 infants and young children in the composition of the present invention. Saliva sample collection was facilitated using foam-tipped swabs (5 swabs per subject) since said subjects were not capable of delivering 1-2 mL of saliva directly into a collection device. A small amount of sugar was used to stimulate the secretion of saliva from young children. Immediately following sample collection, scissors were used to cut the foam tips of each swab into a collection device containing the composition (2 mL) of the present invention, comprised of 4% SDS, 50 mM LiCDTA, 250 mM LiCl, adjusted to pH 6.8. The samples were vigorously shaken and stored at room temperature (RT). Following storage at RT for up to a week, the samples were heated at 50° C. for 1 hour in the presence of proteinase K. Saliva/composition was recovered from the foam tips by low-speed centrifugation as follows. The tips were transferred into the barrel of a 5 mL plastic syringe placed inside a 15 mL conical tube, which was subjected to low-speed centrifugation. The recovered liquid was pooled with the sample remaining in the collection device. To extract RNA from saliva samples, aliquots were heated at 90° C. for 15 min, SDS was precipitated with potassium chloride and, after the precipitate was removed by centrifugation, nucleic acids were precipitated from the supernatant with 2 volumes of cold 95% ethanol.

A portion of each precipitated nucleic acid sample from 11 subjects was used as template in Reverse Transcriptase-PCR (RT-PCR) analysis using primers specific for human 18S ribosomal RNA. Specifically, a portion of precipitated nucleic acid sample from each subject was treated with DNase to remove DNA prior to the Reverse Transcriptase step. The DNA-free sample was then mixed with random hexanucleotide primers and M-MVL reverse transcriptase to synthesize complementary DNA (cDNA). Finally, the cDNA was diluted 10-fold and mixed with human-specific primers (human 18S-165 forward 5' gtgggagcgatttgtctggtt and human 18S-165 reverse 5' ggacatctaagggcatcacag), Taq DNA polymerase and SybrGreen for quantitative real-time PCR analysis. The Ct (Crossing Threshold) values, as shown in Table VII, are inversely proportional to the amount of 18S RNA in the sample. RNA purified from a human colon carcinoma cell line, HCT-116, served as a positive control for RT-PCR analysis. Negative controls include reactions in which no M-MVL RT (-RT) or no cDNA/template was added.

TABLE VII

Real time-PCR with primers specific for human 18S ribosomal RNA.

| Saliva Sample | Age of subject | Ct value | −RT Ct value |
|---|---|---|---|
| Subject 1 | 3 years | 11.88 | 28.27 |
| Subject 2 | 5 years | 12.88 | 23.27 |
| Subject 3 | 25 months | 14.42 | 26.68 |

TABLE VII-continued

Real time-PCR with primers specific for human 18S ribosomal RNA.

| Saliva Sample | Age of subject | Ct value | −RT Ct value |
|---|---|---|---|
| Subject 4 | 3 years | 11.46 | 27.53 |
| Subject 5 | 4 years | 6.17 | 23.0 |
| Subject 6 | 6 years | 7.74 | 25.99 |
| Subject 7 | 8 years | 5.96 | 22.27 |
| Subject 8 | 4 years | 11.7 | 27.02 |
| Subject 9 | 5 months | 10.47 | 28.55 |
| Subject 10 | 15 months | 8.52 | 26.01 |
| Subject 11 | 7 years | 14.82 | 24.2 |
| HCT116 cell line: Positive control | | 2.83 | 14.17 |
| No template (no cDNA): Negative control | | | 21.49 |

Conclusions

These examples demonstrate the efficacy of the composition of the present invention for stabilizing RNA in samples of saliva collected non-invasively from infants and young children, i.e. individuals not capable of expectorating saliva directly into a collection device. Large amounts of human RNA, suitable for RT-PCR analysis, can be recovered from the saliva of said 'non-spitters'.

Example 16: Protocol for Obtaining from the Nasal Cavity of Subjects a Novel Source of Human RNA To collect anterior nasal or nasopharyngeal samples from a subject, a variety of implements may be used. Mucosal cells may be scraped using rigid or flexible brushes, swabs, or plastic/wood scrapers and cells may be flushed from the nasal cavity by introducing a liquid (e.g., saline) and recovering the liquid. For example, a rigid swab/brush can be placed in the anterior of the nose and a flexible swab/brush into the posterior nasopharyngeal cavity and used to collect mucosal secretions and to gently rub off cells from the mucosal membrane. Samples collected with said liquid and/or implement(s) can be delivered into a collection device containing the composition of the present invention. In situations where it is desirable to introduce a volume of said liquid that is greater than the volume of the composition, a correspondingly larger amount of composition of the present invention would be provided. A cutting device (e.g. scissors) may be used to shorten the length of a swab's/applicator's handle to permit closure of the collection device. Alternately, swabs or brushes with handles that snap under pressure, as well as swabs or brushes with a moulded breakpoint in the handle/shaft, can be used to facilitate sample collection. The 'full length' handle facilitates the collection of a sample and shortening of the swab/brush at the engineered break point permits a better fit into the collection device. It is also feasible to recover RNA from tissue samples taken from the nasal cavity. Fresh tissue specimens/biopsies (e.g., normal nasal mucosa or nasal polyp tissue) obtained from patients undergoing rhinoplasty or endoscopic sinus surgery can be collected in the composition of the present invention for subsequent RNA isolation.

The collection of a nasal sample (anterior nasal or nasopharyngeal) from an infant or child generally corresponds to the procedures used for adult humans. It will be clear to the skilled worker that the swab or implement selected to collect such samples must 1) be appropriately sized and shaped to fit within and reach the intended cavity (e.g. nostril, nasopharyngeal cavity), 2) be made from materials considered safe (e.g. free of chemical residues) and clean/sterile (e.g. nucleic acid-free), and 3) have a handle with appropriate flexibility/rigidity and length to facilitate sample collection. If the sample collection implement is a swab, the end of the swab intended to collect sample (e.g. foam mitt) should be tightly adhered to the handle.

Once the nasal secretion, scraping, and/or tissue is collected and introduced into the collection device/container, the sample is immediately mixed with the composition of the present invention. The RNA-containing sample can be maintained at room temperature for months. A portion of the RNA-containing sample in aqueous solution can be used as a RNA template for a reverse transcription (RT) reaction to produce complementary DNA (cDNA), which can then be used in a PCR reaction.

Example 17: Stability of RNA in Human Nasal Samples at Room Temperature for 4 Weeks In this example, the composition comprised 4% SDS, 50 mM LiCDTA, 250 mM LiCl, adjusted to pH 6.8. Anterior nasal samples were collected with 2 foam-tipped swabs per subject. Immediately following sample collection, scissors were used to cut the foam tips of each swab into a collection device containing the composition (2 mL) of the present invention. The samples were vigorously shaken and stored at room temperature (RT). Following 1 day and 4 weeks storage at RT, an aliquot from each sample was analysed. To extract RNA from nasal samples, the aliquots were heated at 50° C. for 1 hour in the presence of proteinase K, then at 90° C. for 15 min. SDS was precipitated with potassium chloride and, after the precipitate was removed by centrifugation, nucleic acids were precipitated from the supernatant with 2 volumes of cold 95% ethanol.

A portion of each precipitated nucleic acid sample from 7 subjects was used as template in Reverse Transcriptase-PCR (RT-PCR) analysis using primers specific for human 18S ribosomal RNA. Specifically, a portion of precipitated nucleic acid sample from each subject was treated with DNase to remove DNA prior to the Reverse Transcriptase step. The DNA-free sample was then mixed with random hexanucleotide primers and M-MVL reverse transcriptase to synthesize complementary DNA (cDNA). Finally, the cDNA was diluted 10-fold and mixed with human-specific primers (human 18S-165 forward 5' gtggagcgatttgtctggtt and human 18S-165 reverse 5' ggacatctaagggcatcacag), Taq DNA polymerase and SybrGreen for quantitative real-time PCR analysis. The Ct (Crossing Threshold) values, as shown in Table VIII, are inversely proportional to the amount of 18S RNA in the sample. RNA purified from a human colon carcinoma cell line, HCT-116, served as a positive control for RT-PCR analysis. Negative controls include reactions in which no M-MVL RT (-RT) or no cDNA/template was added.

TABLE VIII

Real time-PCR with primers specific for human 18S ribosomal RNA.

| Nasal Sample | 1 day aliquot Ct value | 1 day aliquot −RT Ct value | 4 week aliquot Ct value | 4 week aliquot −RT Ct value |
| --- | --- | --- | --- | --- |
| Subject 1 | 13.04 | 30.62 | 14.81 | 28.65 |
| Subject 2 | 15.21 | 31.64 | 18.4 | 29.16 |
| Subject 3 | 15.63 | 31.51 | 12.89 | 28.08 |
| Subject 4 | 11.42 | 28.89 | 12.58 | 27.49 |
| Subject 5 | 15.26 | 31.83 | 15.69 | 27.67 |
| Subject 6 | 14.06 | 30.62 | 13.34 | 28.18 |
| Subject 7 | 14.68 | 30.04 | 15.42 | 28.46 |
| HCT116 cell line: Positive control | 4.92 | 35.37 | 4.92 | 27.50 |
| No template (no cDNA): Negative control | 27.12 | | 29.23 | |

Conclusions

This example demonstrate the efficacy of the composition of the present invention for stabilizing RNA in samples collected from the nasal cavity for long periods of time at room temperature. After 4 weeks, anterior nasal samples from 7 subjects showed no significant change in the Ct value for human 18S ribosomal RNA (as shown in Table VIII). Importantly, this example demonstrates that the nasal cavity is novel source of human RNA.

Example 18: Protocol for Obtaining Saliva from a Human Subject

This example, as shown in FIG. 15, provides one example of the steps that may be followed to collect saliva from a subject.

Note that, on average, it can take approximately one minute to provide a sample of saliva when sugar is used. If user has difficulty making enough saliva, a little more sugar can be used. It is desirable to provide the sample quickly, finishing giving the sample within five minute. Sugar substitutes may also be used. Once the saliva sample is collected in a composition of the present invention, the sample may be stored at room temperature (15-30° C.)

Example 19: Protocol for the Purification of RNA

This example provides one example of the steps that may be followed to isolate RNA from a sample stored using the composition of the present invention. In this example, a composition of the present invention is combined with a sample (such as saliva), and stored at room temperature. The sample/composition mixture can be subsequently processed to purify RNA from the sample, using the following steps:
Reagents and Equipment
1. Neutralizer solution.
2. Ethanol solutions: 70% and 80% (room temperature), 95% (−20° C.).
3. Qiagen RNeasy Micro Kit (Cat. No. 74004) and instructions. Components of the RNeasy kit: RLT buffer, MinElute spin column, collection tubes, RW1 buffer, DNase I stock solution, RDD buffer, RPE buffer and RNase-free water. Alternatively, the Qiagen RNeasy Mini Kit (Cat. No. 74104) can be used in combination with the Qiagen RNase-Free DNase Set (Cat. No. 79254).
Steps Prior to Purification
1. When samples combined with a composition of the present invention are received (e.g., in the lab), shake very vigorously for 8 seconds or longer.
2. Samples may be stored at room temperature for up to 8 weeks or stored frozen at −20° C. indefinitely.
3. Prior to purification, incubate the entire sample in the original vial at 50° C. for one hour in a water bath or for 2 hours in an air incubator.

Initial Purification
1. Remove a 250-500 µL aliquot to a 1.5 mL microcentrifuge tube. (1000 µL aliquot should be processed in 2 tubes).
2. Incubate the aliquot at 90° C. for 15 minutes, then cool to room temperature.
3. Add $\frac{1}{25}^{th}$ volume of Neutralizer solution (e.g., 10 µL Neutralizer for a 250 µL sample. Incubate on ice for 10 minutes.
4. Centrifuge at maximum speed (>13,000×g) for 3 minutes.
5. Taking care not to disturb the pellet, carefully remove supernatant to a fresh tube; discard the pellet.
6. Add 2 volumes of cold 95% EtOH (ethanol). Mix thoroughly by inversion, vortexing or shaking.
7. Incubate at −20° C. for 30 minutes.
8. Collect precipitate by centrifugation at maximum speed (>13,000×g) for 3 minutes.
9. Carefully remove and discard the supernatant, taking care to avoid disturbing the pellet.
10. Dissolve the pellet in 350 µL buffer RLT (RNeasy) by vigorous vortexing, taking care to ensure that the pellet is completely dissolved.
11. Add 1 volume (350 µL) of 70% ethanol. Mix well by vortexing.
12. Proceed immediately to the Qiagen RNeasy Sample Purification instructions.

Qiagen RNeasy Purification Procedure
  Start at step #5 of the Qiagen RNeasy MicroKit "Total RNA Isolation from Animal Cells" Protocol (noting the slight modification to elution step #13).
5. Transfer the sample onto an RNeay MinElute spin column in a 2 mL collection tube. Close the lid and centrifuge for 15 sec at >8000×g. Discard the flow-through. Reuse the collection tube in step 6.
6. Add 350 µL of buffer RW1 to the RNeasy MinElute spin column. Close the lid and centrifuge for 15 sec at >8000×g. Discard the flow-through. Reuse the collection tube in step 8.
7. Add 10 µL DNase I stock solution to 70 µL buffer RDD. Mix by gently inverting the tube.
8. Add the DNase I incubation mix (80 µL) directly onto the RNeasy MinElute spin column membrane and incubate on the benchtop for 15 minutes.
9. Add 350 µL buffer RW1 to the RNeasy MinElute spin column. Close the lid and centrifuge for 15 sec at >8000×g. Discard the flow-through and collection tube.
10. Place the RNeasy MinElute spin column into a fresh 2 mL collection tube. Add 500 µL buffer RPE to the spin column. Close the lid and centrifuge for 15 sec at >8000×g. Discard the flow-through. Reuse the collection tube in step 11.
11. Add 500 µL of 80% ethanol to the RNeasy MinElute spin column. Close the lid and centrifuge for 2 minutes at >8000×g. Discard the flow-through and collection tube.
12. Place the RNeasy MinElute spin column into a fresh 2 mL collection tube. Open the lid of the spin column and centrifuge at full speed for 5 minutes. Discard the flow-through and collection tube.
13. Place the RNeasy MinElute spin column into a fresh 1.5 mL collection tube. Add 25 µL of RNase-free water directly to the center of the spin column membrane. Incubate at room temperature for 5 minutes. Close the lid and centrifuge for 1 minute at full speed to elute the RNA.

Example 20: Extraction and Purification Human RNA from Children from Nasal Samples in the Composition of the Present Invention In this example, RT-PCR was used to detect human-specific messenger RNA in RNA recovered from the anterior nasal cavity of 6 young children in the composition of the present invention. Samples were collected using two foam-tipped swabs, one swab per nostril. Specifically, an adult inserted the foam tip into the child's anterior/lower nasal cavity and swabbed the mucosal membrane with the foam tip by moving the swab in a circular motion. The procedure was repeated for the second nostril with a fresh swab. Immediately following sample collection, scissors were used to cut the foam tip of each swab into a collection device containing the composition (2 mL) of the present invention, comprised of 4% SDS, 50 mM LiCDTA, 250 mM LiCl, adjusted to pH 6.8. The samples were vigorously shaken and stored at room temperature (RT).

Following storage at RT for 1-4 days, the samples were heated at 50° C. for 1 hour in the presence of proteinase K. The nasal sample/composition mixture absorbed by the foam tips was recovered by low-speed centrifugation as follows. The foam tips (2 per child) were transferred into the barrel of a 5 mL plastic syringe placed inside a 15 mL conical tube, which was subjected to low-speed centrifugation. The nasal sample/composition recovered from the foam tips into the 15 mL conical tube was pooled with the nasal sample/composition still in the collection device. To extract RNA from nasal samples, aliquots (500 µL) were heated at 90° C. for 15 min, SDS was precipitated with potassium chloride, the precipitate was removed by centrifugation, and nucleic acids were precipitated from the resultant supernatant with 2 volumes of cold 95% ethanol. The final nucleic acid pellet was dissolved in ribonuclease-free water.

A portion of each precipitated nucleic acid sample from 6 children was used as template in Reverse Transcriptase-PCR (RT-PCR) analysis with primers specific for human 18S ribosomal RNA (18S rRNA). Specifically, a portion of precipitated nucleic acid sample from each subject was treated with DNase to remove DNA prior to the Reverse Transcriptase step. The DNA-free sample was then mixed with random hexanucleotide primers and M-MVL reverse transcriptase to synthesize complementary DNA (cDNA). Finally, the cDNA was diluted 10-fold and mixed with 18S rRNA primers (18S-165 forward 5' gtggagcgatttgtctggtt and 18S-165 reverse 5' ggacatctaagggcatcacag), Taq DNA polymerase and Syto9 for quantitative real-time PCR analysis. The Ct (Crossing Threshold) values, as shown in Table IX, are inversely proportional to the amount of 18S rRNA in the sample. RNA purified from a human colon carcinoma cell line, HCT-116, served as a positive control for RT-PCR analysis. Negative controls include reactions in which no M-MVL RT (-RT) or no cDNA/template was added.

TABLE IX

Real time-PCR with primers specific for 18S ribosomal RNA.

| Nasal Sample | Age of subject | Ct value | −RT Ct value |
|---|---|---|---|
| Subject 1 | 6 years | 7.27 | 31.2 |
| Subject 2 | 6 years | 12.13 | 31.29 |
| Subject 3 | 5 years | 12.8 | 31.02 |
| Subject 4 | 4 years | 18.27 | 30.72 |
| Subject 5 | 7 years | 12.9 | 31.43 |
| Subject 6 | 4 years | 17.08 | 29.78 |
| HCT116 cell line: Positive control | | 5.79 | 29.84 |
| No template (no cDNA): Negative control | | 29.31 | |

Conclusions

This example demonstrates the efficacy of the composition of the present invention for extracting and stabilizing RNA in anterior nasal samples from children. Large amounts of human RNA, suitable for RT-PCR analysis, can be recovered from children with this minimally invasive collection method and stabilizing composition.

Example 22: Protocol for Obtaining Sample from the Nasal and Oral Cavities of Livestock Nasal and oral samples can be collected from livestock, including beef cattle, dairy cows, sheep, goats, hogs, poultry and horses. In a specific, non-limiting example, nasal or oral samples can be readily collected from dairy cows (*Bovidae Bos taurus*) while the cow is standing in stanchions in the milking parlour, or while tied in pens. Depending on the age, size, and/or strength of the animal, the assistance of a handler may, or may not, be required to restrain/steady the animal's head for nasal sample collection or open the animal's mouth for oral sample collection. A variety of implements may be used to collect nasal and oral samples from livestock. For example, implement(s) the same as or similar to those described above in Example 16 may be used. The implement(s) should be appropriately sized, taking into account the dimensions of the cavity into which the implement will be inserted. It will be clear that veterinary assistance may not be need using this method.

Example 23: RNA Stabilized in Nasal Samples from Holstein Dairy Cows (*Bovidae Bos*) Using the Composition of the Present Invention In this example, the composition comprised 4% SDS, 50 mM LiCDTA, 250 mM LiCl, adjusted to pH 6.8. Anterior nasal samples were collected with one large foam-tipped swab (head length 2.6 cm, head width 1.2 cm, swab length 15.1 cm) per cow. In each case, the cow's head was steadied by a 'handler' while a 'collector' quickly inserted the foam tip of the swab into the cow's nostril, specifically the anterior nose. The foam tip was quickly wiped against the mucous membrane of the anterior nose/nostril and then withdrawn. For the most part, a 'handler' is not needed for the collection of nasal samples from calves. Immediately following collection, scissors were used to cut the foam tip of the swab into a collection device containing the composition (2 mL) of the present invention. The samples were vigorously shaken and stored at room temperature (RT).

Following 16 days at RT, the sample/composition mixture absorbed by the foam tip was recovered by low-speed centrifugation as follows. Forceps were used to transfer the foam tip into the barrel of a 5 mL plastic syringe situated inside a 15 mL conical tube, which was subjected to low-speed centrifugation. The sample/composition recovered from foam tips by this process was pooled with the sample/composition in the collection device. To extract RNA from nasal samples, each aliquot was heated at 50° C. for 1 hour in the presence of proteinase K and then 90° C. for 15 min, SDS was precipitated with potassium chloride and, after the precipitate was removed by centrifugation, nucleic acids were precipitated from the supernatant with 2 volumes of cold 95% ethanol. The final nucleic acid pellet was dissolved in ribonuclease-free water.

A portion of each precipitated nucleic acid sample from 8 dairy cows was used as template in Reverse Transcriptase-PCR (RT-PCR) analysis using primers for 18S ribosomal RNA. Specifically, a portion of precipitated nucleic acid sample from each dairy cow was treated with DNase to remove DNA prior to the Reverse Transcriptase step. The DNA-free sample was then mixed with random hexanucleotide primers and M-MVL reverse transcriptase to synthesize complementary DNA (cDNA). Finally, the cDNA was diluted 10-fold and mixed with 18S ribosomal RNA primers (18S-165 forward 5' gtgggagcgatttgtctggtt and 18S-165 reverse 5' ggacatctaagggcatcacag), Taq DNA polymerase and Syto9 for quantitative real-time PCR analysis. The Ct (Crossing Threshold) values, as shown in Table X, are inversely proportional to the amount of 18S ribosomal RNA in the sample. HCT-116 RNA served as a positive control for RT-PCR analysis. Negative controls include reactions in which no M-MVL RT (-RT) or no cDNA/template was added.

TABLE X

| Nasal Sample | Ct value | -RT Ct value |
| --- | --- | --- |
| Cow 1 | 15.31 | 31.75 |
| Cow 2 | 13.94 | 32.17 |
| Cow 3 | 19.02 | 30.64 |
| Cow 4 | 13.1 | 28.38 |
| Cow 5 | 14.14 | 31.31 |
| Cow 6 | 16.69 | 31.4 |
| Cow 7 | 18.68 | 31.03 |
| Cow 8 | 11.49 | 31.83 |
| HCT116 cell line: Positive control | 5.95 | 27.07 |
| No template (no cDNA): Negative control | 31.53 | |

Conclusions

This example demonstrates the efficacy of the composition of the present invention for extracting and stabilizing RNA in samples collected from the anterior nasal cavity of dairy cows (as shown in Table X). Importantly, this example demonstrates that the nasal cavity is a novel and abundant source of messenger RNA in cattle.

REFERENCES

1. Analysis of gene expression profiles of normal human nasal mucosa and nasal polyp tissues by SAGE. Lee J Y et al. (2006) J Allergy Clin Immunol 118(1): 134-142.
2. Optimization of the Weck-Cel collection method for quantitation of cytokines in mucosal secretions. Rohan L C et al. (2000) Clin Diagn Lab Immunol 7(1): 45-48.
3. Development and evaluation of a novel loop-mediated isothermal amplification method for rapid detection of severe acute respiratory syndrome coronavirus. Thai H T C et al. (2004) J Clin Microbiol 42(5): 1956-1961.
4. World Health Organization Multicentre Collaborative Network for Severe Acute Respiratory Syndrome Diagnosis (2003). A multicentre collaboration to investigate the cause of severe acute respiratory syndrome. Lancet 361: 1730-1733.
5. Evaluation of reverse transcription-PCR assays for rapid diagnosis of severe acute respiratory syndrome associated with a novel coronavirus. Yam W C et al. (2003) J Clin Microbiol 141: 4521-4524.
6. Epidemiological determinants of spread of causal agent of severe acute respiratory syndrome in Hong Kong. Donnelly C A et al. (2003) Lancet 361: 1761-1766.
7. Evaluation of serological and virological tests in the diagnosis of clinical and subclinical measles virus infections during an outbreak of measles in the Netherlands. van Binnendijk R S et al. (2003) J Infectious Dis 188: 898-903.

8. Investigation of optimal specimen type and sampling time for detection of measles virus RNA during a measles epidemic. Riddell M A et al. (2001) J Clin Microbiol 39(1): 375-376.
9. Evaluation of events occurring at mucosal surfaces: techniques used to collect and analyze mucosal secretions and cells. Guy B (2002) Clin Diagn Lab Immunol 9(4): 753-762.
10. Initial viral load and the outcomes of SARS. Chu C-M et al. (2004) CMAJ 171(11): 1349-1352.
11. Clinical progression and viral load in a community outbreak of coronavirus-associated SARS pneumonia: a prospective study. Peiris J S et al. (2003) Lancet 361: 1767-1772.
12. Development of a western blot assay for detection of antibodies against coronavirus causing severe acute respiratory syndrome. He Q et al. (2004) Clin Diagn Lab Immunol 11(2): 417-422.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A phenol-free method for preserving ribonucleic acid from a biological sample comprising the steps of:
   a. obtaining the sample from a subject;
   b. contacting the sample with a composition comprising an anionic detergent, wherein the anionic detergent is at a concentration of 1% to 8%, and a buffering agent at a pH of about 5 to about 8.2 to form a mixture;
   c. storing the mixture at room temperature; and
   d. heating the mixture, wherein the mixture is heated at a temperature of greater than or about equal to 50° C.,
wherein the composition stabilizes the ribonucleic acid at room temperature.

2. The method of claim 1, wherein step d further comprises contacting the mixture with a protease.

3. The method of claim 2, wherein the protease is proteinase K.

4. The method of claim 1 further comprising heating the mixture, wherein the mixture is heated at a temperature of greater than or equal to about 90° C. before or after heating step d.

5. The method of claim 1, wherein the anionic detergent is sodium dodecyl sulphate, sodium lauroyl sarcosinate, lithium dodecyl sulphate or sodium 1-octane sulfonic acid.

6. The method of claim 1, wherein the anionic detergent is sodium dodecyl sulphate or sodium sarcosinate.

7. The method of claim 1, wherein the buffering agent is at a pH of about 5.1 to about 7.

8. The method of claim 1, wherein the buffering agent is sodium cyclohexane diaminetetraacetate (CDTA), N,N-bis(2-hydroxyethyl)-2-aminoethanesulfonic acid (BES), 4-(2-Hydroxyethyl)piperazine-1-ethanesulfonic acid (HEPES), acetic acid or acetate (e.g. sodium acetate), citric acid or citrate, malic acid, phthalic acid, succinic acid, histidine, pyrophosphoric acid, maleic acid, cacodylic acid, ββ'-Dimethylglutaric acid, carbonic acid or carbonate, 5(4)-Hydroxymethylimidazole, glycerol 2-phosphoric acid, ethylenediamine, imidazole, arsenic acid, phosphoric acid or phosphate, sodium acetate, 2:4:6-collidine, 5(4)-methylimidazole, N-ethylmorpholine, triethanolamine, diethylbarbituric acid, tris(hydroxymethyl)aminomethane (Tris), 3-(N-Morpholino)propanesulfonic acid; 4-morpholinepropanesulfonic acid (MOPS), 2-morpholinoethanesulfonic acid (MES), piperazine-1,4-bis(2-ethanesulfonic acid) (PIPES), N-[tris(hydroxymethyl)methyl]-2-aminoethanesulfonic acid (TES), 4-(2-Hydroxyethyl)piperazine-1-propanesulfonic acid (EPPS), N-(2-acetamido)-2-aminoethanesulfonic acid (ACES), or combinations thereof.

9. The method of claim 1, wherein the buffering agent is a phosphate buffer, a carbonate buffer, an ethylenediamine buffer or an imidazole buffer.

10. The method of claim 1, wherein the buffering agent is CDTA or citric acid.

11. The method of claim 1, wherein the sample is a bodily fluid or a bodily tissue from a mammal.

12. The method of claim 11, wherein the mammal is a human or a cow.

13. The method of claim 1, wherein the sample is from a human; a non-human primate; livestock including cattle, pigs, sheep, goats or domestic birds including chicken, turkey, pheasant, duck or geese; game or wild animals including deer, elk, moose, fish, birds or bears; laboratory or companion animals including non-human primates, rodents including mice, rats, rabbits, guinea pigs, gerbils or hamsters; dogs; cats; fish; snakes; lizards; turtles; a horse; plants; plant parts; cell lines; soil microorganisms; sewage microorganisms; or pathogenic microorganisms including virus, bacteria or parasites.

14. The method of 1, wherein the composition stabilizes the ribonucleic acid at room temperature for one or more of the following time periods:
at least about one day, two days, three days, four days, five days, six days, one week, two weeks, three weeks, four weeks, five weeks, six weeks, seven weeks or eight weeks, about one day to about eight weeks, or greater than about eight weeks.

15. The method of 14, wherein the composition stabilizes the ribonucleic acid at room temperature for about one day to about eight weeks at room temperature.

16. The method of claim 1, wherein the buffering agent is at a pH of about 5.5 to about 7.5.

17. The method of claim 1, wherein the buffering agent is at a pH of about 6.5 to about 7.0.

18. The method of claim 1, wherein the buffering agent is at a pH of about 6.8.

* * * * *

UNITED STATES PATENT AND TRADEMARK OFFICE
CERTIFICATE OF CORRECTION

| | | |
|---|---|---|
| PATENT NO. | : 10,000,795 B2 | Page 1 of 1 |
| APPLICATION NO. | : 15/160712 | |
| DATED | : June 19, 2018 | |
| INVENTOR(S) | : Hyman Chaim Birnboim et al. | |

It is certified that error appears in the above-identified patent and that said Letters Patent is hereby corrected as shown below:

In the Claims

Column 36, Line 42, Claim 14, delete "of 1" and insert --of claim 1--.

Column 36, Line 50, Claim 15, delete "of 14" and insert --of claim 1--.

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*